United States Patent
Rockweiler et al.

(10) Patent No.: US 10,183,169 B2
(45) Date of Patent: Jan. 22, 2019

(54) SYSTEMS AND METHODS FOR FACILITATING SELECTION OF ONE OR MORE VECTORS IN A MEDICAL DEVICE

(71) Applicant: Cardiac Pacemakers, Inc., St. Paul, MN (US)

(72) Inventors: Holly E. Rockweiler, San Francisco, CA (US); Sunipa Saha, Shoreview, MN (US); Keith L. Herrmann, Minneapolis, MN (US); Yinghong Yu, Shoreview, MN (US); Joel A. Krueger, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/454,824

(22) Filed: Mar. 9, 2017

(65) Prior Publication Data
US 2017/0173342 A1    Jun. 22, 2017

Related U.S. Application Data

(63) Continuation of application No. 14/670,075, filed on Mar. 26, 2015, now Pat. No. 9,597,515.
(Continued)

(51) Int. Cl.
*A61N 1/00* (2006.01)
*A61N 1/37* (2006.01)
(Continued)

(52) U.S. Cl.
CPC .......... *A61N 1/371* (2013.01); *A61B 5/04011* (2013.01); *A61N 1/056* (2013.01);
(Continued)

(58) Field of Classification Search
CPC ..... A61N 1/371; A61N 1/3712; A61N 1/3686
(Continued)

(56) References Cited

U.S. PATENT DOCUMENTS 6,128,535 A    10/2000    Maarse
6,192,275 B1    2/2001    Zhu et al.
(Continued)

FOREIGN PATENT DOCUMENTS

AU    2015237194 B2    8/2017
CN    103180011 A    6/2013
(Continued)

OTHER PUBLICATIONS

"U.S. Appl. No. 14/670,075, Advisory Action dated Aug. 19, 2016", 3 pgs.
(Continued)

*Primary Examiner* — Amanda Hulbert
*Assistant Examiner* — Philip C Edwards
(74) *Attorney, Agent, or Firm* — Schwegman Lundberg & Woessner, P.A.

(57) ABSTRACT

Systems and methods may facilitate selection of a vector for delivering electrical stimulation to a patient's heart. One illustrative method may include delivering electrical stimulation at a first voltage to each vector in a first set of two or more vectors of a multi-vector medical system, determining whether the delivered electrical stimulation at the first voltage resulted in capture for each of the vectors in the first set of two or more vectors, identifying those vectors of the first set of two or more vectors that were determined to result in capture as a second set of vectors, delivering electrical stimulation at a second voltage that is lower than the first voltage to each vector in the second set of vectors, and
(Continued)

determining whether the delivered electrical stimulation at the second voltage resulted in capture for each of the vectors in the second set of vectors.

20 Claims, 14 Drawing Sheets

Related U.S. Application Data

(60) Provisional application No. 61/971,653, filed on Mar. 28, 2014.

(51) Int. Cl.
| | | |
|---|---|---|
| *A61N 1/05* | (2006.01) | |
| *A61N 1/362* | (2006.01) | |
| *A61N 1/365* | (2006.01) | |
| *A61N 1/368* | (2006.01) | |
| *A61B 5/04* | (2006.01) | |

(52) U.S. Cl.
CPC ............ *A61N 1/368* (2013.01); *A61N 1/3622* (2013.01); *A61N 1/3684* (2013.01); *A61N 1/3686* (2013.01); *A61N 1/36521* (2013.01)

(58) Field of Classification Search
USPC .......................................................... 607/28
See application file for complete search history.

(56) References Cited

U.S. PATENT DOCUMENTS

| 6,226,551 | B1 | 5/2001 | Zhu et al. |
|---|---|---|---|
| 6,615,089 | B1 | 9/2003 | Russie et al. |
| 6,937,901 | B2 | 8/2005 | Zhu et al. |
| 6,978,178 | B2 | 12/2005 | Sommer et al. |
| 7,031,773 | B1 | 4/2006 | Levine et al. |
| 7,299,093 | B2 | 11/2007 | Zhu et al. |
| 7,392,086 | B2 | 6/2008 | Sathaye |
| 8,160,700 | B1 | 4/2012 | Ryu et al. |
| 8,265,736 | B2 | 9/2012 | Sathaye et al. |
| 8,401,646 | B2 | 3/2013 | Stadler et al. |
| 8,744,572 | B1 | 6/2014 | Greenhut et al. |
| 9,597,515 | B2 | 3/2017 | Rockweiler et al. |
| 2006/0074454 | A1 | 4/2006 | Freeberg |
| 2009/0054946 | A1 | 2/2009 | Sommer et al. |
| 2010/0198292 | A1 | 8/2010 | Honeck et al. |
| 2010/0305638 | A1 | 12/2010 | McCabe et al. |
| 2011/0004264 | A1 | 1/2011 | Siejko et al. |
| 2012/0035685 | A1 | 2/2012 | Saha et al. |
| 2012/0078320 | A1 | 3/2012 | Schotzko et al. |
| 2012/0101543 | A1* | 4/2012 | Demmer .............. A61N 1/3686 607/28 |
| 2012/0296387 | A1 | 11/2012 | Zhang et al. |
| 2013/0183182 | A1 | 7/2013 | White, Jr. |
| 2014/0005742 | A1 | 1/2014 | Mahajan et al. |
| 2014/0018872 | A1 | 1/2014 | Siejko et al. |
| 2014/0214104 | A1 | 7/2014 | Greenhut et al. |
| 2015/0273218 | A1 | 10/2015 | Rockweiler et al. |

FOREIGN PATENT DOCUMENTS

| CN | 106413806 A | 2/2017 |
|---|---|---|
| IN | 201617035674 A | 3/2017 |
| JP | 2012531288 A | 2/2012 |
| JP | 2017512584 A | 5/2017 |
| WO | WO-2015148995 A1 | 10/2015 |

OTHER PUBLICATIONS

"U.S. Appl. No. 14/670,075, Final Office Action dated Jun. 17, 2016", 10 pgs.
"U.S. Appl. No. 14/670,075, Non Final Office Action dated Jan. 13, 2016", 8 pgs.
"U.S. Appl. No. 14/670,075, Notice of Allowance dated Nov. 8, 2016", 8 pgs.
"U.S. Appl. No. 14/670,075, Response filed Apr. 5, 2016 to Non Final Office Action dated Jan. 13, 2016", 8 pgs.
"U.S. Appl. No. 14/670,075, Response to Final Office Action dated Jun. 17, 2016", 8 pgs.
"Australian Application Serial No. 2015237194, First Examiner Report dated Feb. 9, 2017", 3 pgs.
"International Application Serial No. PCT/US2015/023128, International Preliminary Report on Patentability dated Oct. 13, 2016", 9 pgs.
"International Application Serial No. PCT/US2015/023128, International Search Report dated Jun. 17, 2015", 5 pgs.
"International Application Serial No. PCT/US2015/023128, Written Opinion dated Jun. 17, 2015", 7 pgs.
"Australian Application Serial No. 2015237194, Response filed Mar. 16, 2017 to First Examiner Report dated Feb. 9, 2017", 16 pgs.
"European Application Serial No. 15716938.4, Response filed Jun. 8, 2017 to Communication Pursuant to Rules 161(1) and 162 EPC dated Dec. 6, 2016", 14 pgs.
"Japanese Application Serial No. 2016-559634, Examiners Decision of Final Refusal dated May 8, 2018", w/ English translation, 6 pgs.
"Japanese Application U.S. Appl. No. 2016-559634, Office Action dated Aug. 8, 2017", w/ English translation, 11 pgs.
"Japanese Application Serial No. 2016-559634, Response filed Nov. 8, 2017 to Office Action dated Aug. 8, 2017", w/ claims in English, 11 pgs.

* cited by examiner

| Vector — 1010 | Quick Threshold — 1020 | Threshold — 1030 |
|---|---|---|
| LV2-RV | ≤ 2.5V | 1.2 V |
| LV2-LV3 | 4.0V > Tr > 2.5V | 2.7 V |
| LV2-CAN | > 4.0V | ... |
| LV2-LV4 | > 2.5V | ... |

FIG. 10

Auto Vector Select

STARTING TEST VALUES

1st Voltage Level [ ] — 1120
2nd Voltage Level [ ] — 1122
3rd Voltage Level [ ] — 1124

1st Step Value [ ] — 1126
2nd Step Value [ ] — 1128

△ — 252 Start LV Threshold Search

| | RV-LV Delay (ms) ▼ | Impedance ▼ | PS Threshold ▼ | Quick Threshold ▼ |
|---|---|---|---|---|
| LV2-RV | 130 ms | 753 Ω | NO PS | |
| LV2-LV3 | 120 ms | 634 Ω | NO PS | |
| LV2-Can | 100 ms | 863 Ω | NO PS | |
| LV2-LV4 | 90 ms | >1000 Ω | NO PS | |
| LV1-Can | 120 ms | 586 Ω | PS @ 7.5 V | |
| LV1-LV1 | 100 ms | 690 Ω | PS @ 7.5 V | |
| LV1-LV2 | 80 ms | 756 Ω | PS @ 7.5 V | |

FIG. 11

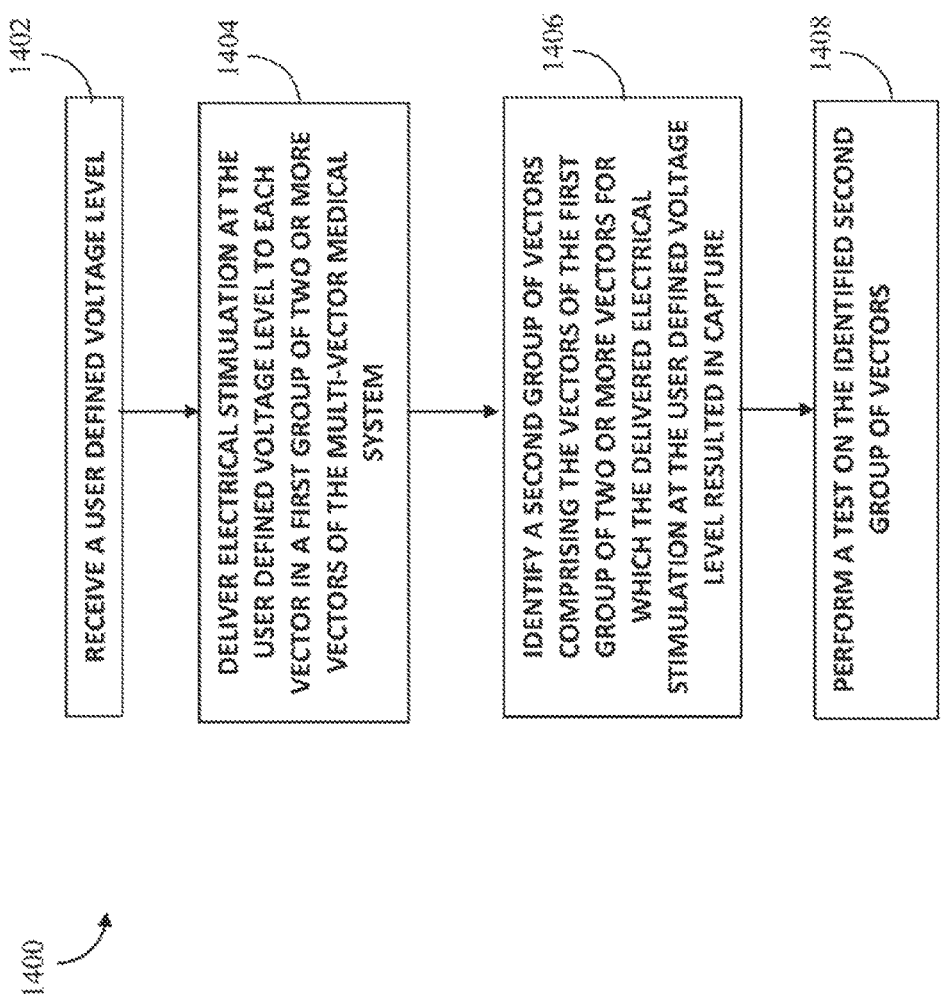

SYSTEMS AND METHODS FOR FACILITATING SELECTION OF ONE OR MORE VECTORS IN A MEDICAL DEVICE

CLAIM OF PRIORITY

This application is a continuation of U.S. application Ser. No. 14/670,075, filed Mar. 26, 2015, which claims priority under 35 U.S.C. § 119 to U.S. Provisional Application Ser. No. 61/971,653, filed Mar. 28, 2014, the entirety of each of which is incorporated herein by reference.

TECHNICAL FIELD

The present disclosure relates generally to systems and methods for configuring an implantable medical device, and more specifically for assessing and selecting one or more vectors for delivery of electrical stimulation to a patient by the implantable medical device.

BACKGROUND

Medical devices have been developed that provide various types of electrical stimulation therapy to a patient including, for example, cardiac stimulation therapy, neuro-stimulation therapy, baroreceptor stimulation therapy, and/or other forms of electrical stimulation therapy. In some instances, multiple electrodes are available, and the electrodes may be configured in a number of different combinations for sensing electrical activity and/or delivering the electrical stimulation therapy. Using different combinations of electrodes for sensing electrical activity may produce different sensed signals. Using different combinations of electrodes for delivering electrical stimulation therapy may produce different effectiveness of the electrical stimulation therapy. Each electrode combination can be referred to as a "vector". In some systems, the number of available "vectors" can be relatively large. In such systems, assessing each vector in order to select a satisfactory or best vector for sensing and/or delivering electrical stimulation therapy can be time consuming, and in some cases bothersome to the patient.

SUMMARY

The present disclosure relates generally to systems and methods for assessing a plurality of vectors in a medical device system, and in some cases, aiding in the selection of one or more of the vectors for sensing electrical activity and/or delivering electrical stimulation therapy based on the assessment. In some cases, the present disclosure may provide systems and methods for efficiently identifying suitable vectors for sensing cardiac electrical data and/or delivering electrical stimulation therapy. Reducing the amount of time and effort required to identifying suitable vectors can help reduce procedure time for implanting and/or configuring an implantable medical device, and in some cases can help reduce discomfort to the patient.

In one embodiment, a method for determining a capture threshold for one or more vectors of a multi-vector medical system comprises delivering electrical stimulation at a first voltage to each vector in a first set of two or more vectors of the multi-vector medical system, and determining whether the delivered electrical stimulation at the first voltage resulted in capture for each of the vectors in the first set of two or more vectors. In at least some embodiments, the method may further comprise identifying those vectors of the first set of two or more vectors that were determined to result in capture as a second set of vectors and delivering electrical stimulation at a second voltage that is lower than the first voltage to each vector in the second set of vectors. In some additional embodiments, the method may comprise determining whether the delivered electrical stimulation at the second voltage resulted in capture for each of the vectors in the second set of vectors.

Additionally, or alternatively, in the above embodiments, the method may further comprise, for each vector in the second set of vectors, repeatedly delivering electrical stimulation at successively lower voltages and determining at each voltage whether the delivered electrical stimulation resulted in capture, until the capture threshold is determined.

Additionally, or alternatively, in any of the above embodiments, the first voltage is user defined.

Additionally, or alternatively, in any of the above embodiments, the first voltage is user defined and is accepted via a menu on a user display.

Additionally, or alternatively, in any of the above embodiments, if the delivered electrical stimulation at the first voltage does not result in capture for any of the vectors in the first set of two or more vectors, raising the first voltage and returning to the first delivering step.

Additionally, or alternatively, in any of the above embodiments, the first voltage is between 1.0 and 5.0 volts.

Additionally, or alternatively, in any of the above embodiments, the first voltage is between 1.5 and 4.5 volts.

Additionally, or alternatively, in any of the above embodiments, the first voltage is between 2.0 and 3.5 volts.

Additionally, or alternatively, in any of the above embodiments, the first set of two or more vectors is a subset of all available vectors of the multi-vector medical system.

Additionally, or alternatively, in any of the above embodiments, the method may further comprise selecting the first set of two or more vectors from all available vectors of the multi-vector medical system.

Additionally, or alternatively, in any of the above embodiments, the method may further comprise generating one or more parameters for each of the available vectors of the multi-vector medical system, and selecting the first set of two or more vectors from all available vectors of the multi-vector medical system based, at least in part, on the one or more generated parameters.

Additionally, or alternatively, in any of the above embodiments, the one or more parameters include an impedance, a delay, or a phrenic stimulation value.

Additionally, or alternatively, in any of the above embodiments, the method may further comprise identifying those vectors of the second set of vectors that were determined to result in capture as a third set of vectors, delivering electrical stimulation at a third voltage that is lower than the second voltage to each vector in the third set of vectors, and determining whether the delivered electrical stimulation at the third voltage resulted in capture for each of the vectors in the third set of vectors.

Additionally, or alternatively, in any of the above embodiments, the method may further comprises, for each vector in the third set of vectors, repeatedly delivering electrical stimulation at successively lower voltages and determining at each voltage whether the delivered electrical stimulation resulted in capture, until the capture threshold is determined.

In another embodiment, a medical system capable of stimulating a heart of a patient using two or more vectors comprise three or more electro-stimulation electrodes, a pulse generator configured to deliver electrical stimulation pulses using each of the two or more vectors via the electro-stimulation electrodes, and a controller coupled to the pulse generator. In at least some embodiments, the controller is configured to cause the pulse generator to deliver an electrical stimulation pulse at a first voltage to each vector in a first set of two or more vectors, determine whether the delivered electrical stimulation pulse at the first voltage resulted in capture for each of the vectors in the first set of two or more vectors, identify those vectors of the first set of two or more vectors that were determined to result in capture as a second set of vectors, deliver electrical stimulation at a second voltage that is lower than the first voltage to each vector in the second set of vectors, and determine whether the delivered electrical stimulation at the second voltage resulted in capture for each of the vectors in the second set of vectors.

Additionally, or alternatively, in the above embodiment, for each vector in the second set of vectors, the controller is configured to repeatedly deliver electrical stimulation at successively lower voltages and determine at each voltage whether the delivered electrical stimulation resulted in capture, until the capture threshold is determined.

Additionally, or alternatively, in any of the above embodiments, the controller is further configured to receive a value for the first voltage from a user.

Additionally, or alternatively, in any of the above embodiments, comprising a display for receiving the value for the first voltage from the user.

In yet another embodiment, a method for determining a capture threshold using electrical stimulation pulses comprises successively stepping down a voltage of the electrical stimulation pulses using a first voltage step until capture is no longer detected, and raising the voltage, and then successively stepping down the voltage of the electrical stimulation pulses using a second voltage step until capture is no longer detected, wherein the second voltage step is less than the first voltage step.

Additionally, or alternatively, in the above embodiment, at least one of the first voltage step and the second voltage step are user definable via a menu on a display.

In still another embodiments, a medical system capable of stimulating a heart of a patient using two or more vectors comprises three or more electro-stimulation electrodes, a pulse generator configured to deliver electrical stimulation pulses using each of the two or more vectors via the electro-stimulation electrodes, and a controller coupled to the pulse generator. In at least some embodiments, the controller is configured to cause the pulse generator to deliver an electrical stimulation pulse at a first voltage to each vector in a first set of two or more vectors, determine whether the delivered electrical stimulation pulse at the first voltage resulted in capture for each of the vectors in the first set of two or more vectors, identify those vectors of the first set of two or more vectors that were determined to result in capture as a second set of vectors, deliver electrical stimulation at a second voltage that is lower than the first voltage to each vector in the second set of vectors, and determine whether the delivered electrical stimulation at the second voltage resulted in capture for each of the vectors in the second set of vectors.

Additionally, or alternatively, in any above embodiment, for each vector in the second set of vectors, the controller is configured to repeatedly deliver electrical stimulation at successively lower voltages and determine at each voltage whether the delivered electrical stimulation resulted in capture, until the capture threshold is determined.

Additionally, or alternatively, in any of the above embodiments, the controller is further configured to receive a value for the first voltage from a user.

Additionally, or alternatively, in any of the above embodiments, the method may further comprise a display for receiving the value for the first voltage from the user.

Additionally, or alternatively, in any of the above embodiments, the controller is further configure to, if the delivered electrical stimulation at the first voltage does not result in capture for any of the vectors in the first set of two or more vectors, raise the first voltage and returning to the first delivering step.

Additionally, or alternatively, in any of the above embodiments, the first voltage is between 1.0 and 5.0 volts.

Additionally, or alternatively, in any of the above embodiments, the first voltage is between 1.5 and 4.5 volts.

Additionally, or alternatively, in any of the above embodiments, the first voltage is between 2.0 and 3.5 volts.

Additionally, or alternatively, in any of the above embodiments, the first set of two or more vectors includes less than all available vectors of the medical system.

Additionally, or alternatively, in any of the above embodiments, the controller is further configured to select the first set of two or more vectors from all available vectors of the medical system.

Additionally, or alternatively, in any of the above embodiments, the controller is further configured to generate one or more parameters for each of the available vectors of the medical system, and select the first set of two or more vectors from all available vectors of the medical system based, at least in part, on the one or more generated parameters.

Additionally, or alternatively, in any of the above embodiments, the one or more parameters includes one or more of an impedance, a delay, and a phrenic stimulation value.

Additionally, or alternatively, in any of the above embodiments, the controller is further configured to identify those vectors of the second set of vectors that were determined to result in capture as a third set of vectors, deliver electrical stimulation at a third voltage that is lower than the second voltage to each vector in the third set of vectors, and determine whether the delivered electrical stimulation at the third voltage resulted in capture for each of the vectors in the third set of vectors.

Additionally, or alternatively, in any of the above embodiments, the controller is further configured to, for each vector in the third set of vectors, repeatedly deliver electrical stimulation at successively lower voltages and determining at each voltage whether the delivered electrical stimulation resulted in capture, until the capture threshold is determined.

Additionally, or alternatively, in any of the above embodiments, the second voltage is lower than the first voltage by a voltage step and the voltage step is settable by a user and has a maximum allowed value.

In another embodiment, a method for determining capture for a plurality of vectors in a multi-vector medical system comprises receiving a user defined voltage level, delivering electrical stimulation at the user defined voltage level to each vector in a first group of two or more vectors of the multi-vector medical system, and identifying a second group of vectors comprising the vectors of the first group of two or more vectors for which the delivered electrical stimulation at the user defined voltage level resulted in capture. In at least some embodiments, the method may additionally comprise performing a test on the identified second group of vectors.

Additionally, or alternatively, in any of the above embodiments, the test comprises a capture threshold test.

Additionally, or alternatively, in any of the above embodiments, performing the capture threshold test comprises performing the capture threshold test with the user defined voltage level as an initial voltage level.

Additionally, or alternatively, in any of the above embodiments, performing the capture threshold test comprises performing the capture threshold test with an initial voltage level less than the user defined voltage level.

Additionally, or alternatively, in any of the above embodiments, performing the capture threshold test comprises performing the capture threshold test with an initial voltage level greater than the user defined voltage level.

Additionally, or alternatively, in any of the above embodiments, the test comprises delivering electrical stimulation at a second voltage to each vector in the second group of vectors of the multi-vector medical system, and determining whether the delivered electrical stimulation at the second voltage resulted in capture for each of the vectors in the second group of vectors.

Additionally, or alternatively, in any of the above embodiments, the method may further comprise identifying those vectors of the second group of vectors that were determined to result in capture as a third group of vectors, delivering electrical stimulation at a third voltage that is lower than the second voltage to each vector in the third group of vectors, and determining whether the delivered electrical stimulation at the third voltage resulted in capture for each of the vectors in the third group of vectors.

Additionally, or alternatively, in any of the above embodiments, the method may further comprise for each vector in the second group of vectors, repeatedly delivering electrical stimulation at successively lower voltages and determining at each voltage whether the delivered electrical stimulation resulted in capture, until a capture threshold is determined.

Additionally, or alternatively, in any of the above embodiments, the second voltage level is the user defined voltage level.

Additionally, or alternatively, in any of the above embodiments, the second voltage level is less than the user defined voltage level.

Additionally, or alternatively, in any of the above embodiments, the second voltage level is greater than the user defined voltage level.

Additionally, or alternatively, in any of the above embodiments, the second voltage level is user defined.

Additionally, or alternatively, in any of the above embodiments, the test comprises successively stepping down a voltage of the electrical stimulation pulses using a first voltage step until capture is no longer detected, and raising the voltage, and then successively stepping down the voltage of the electrical stimulation pulses using a second voltage step until capture is no longer detected, wherein the second voltage step is less than the first voltage step.

Additionally, or alternatively, in any of the above embodiments, at least one of the first voltage step and the second voltage step are user definable via a menu on a display.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 10 is another illustrative table of vectors which may be displayed by the implantable medical system of FIG. 1;

FIG. 11 is a graphical illustration of a GUI that includes an illustrative sortable table of vectors which may be displayed by the implantable medical system of FIG. 1;

FIG. 14 is a flow diagram of another illustrative method that may be implemented by an implantable medical device system such as the implantable medical system of FIG. 1.

Figure 1:
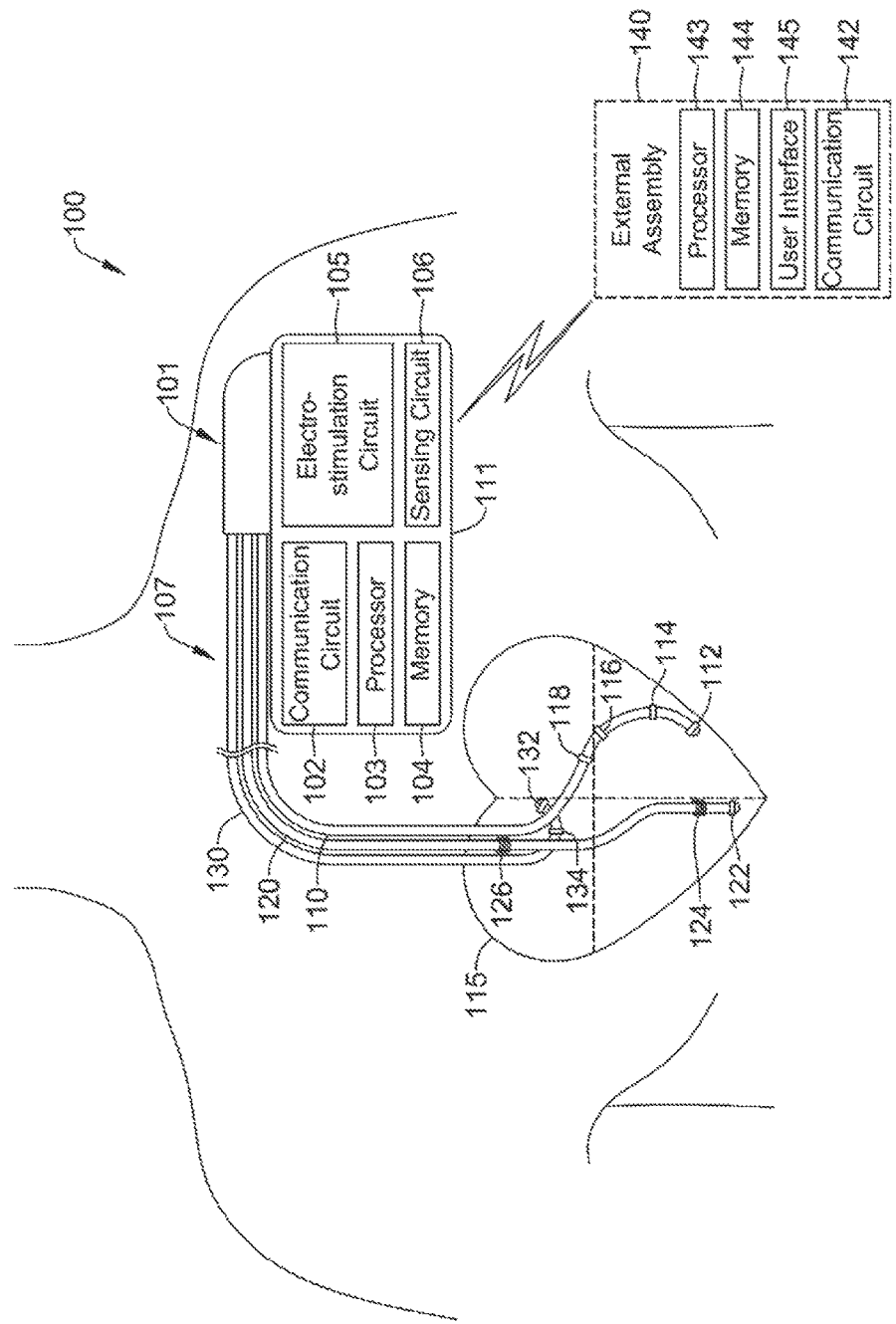
FIG. 1 is a schematic view of an illustrative implantable medical system.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer conduct intrinsic electrical stimulation signals. In other examples, diseased tissue may not conduct the intrinsic signals as quickly as healthy tissue, thereby de-synchronizing the contraction of the heart. For example, portions of the heart muscle may contract earlier or later than other muscle cells of the heart due to the different conductivity of the heart tissue with respect to the intrinsic electrical signals. This un-coordinated contraction can result in a decrease in the flow of blood throughout the rest of the body, causing various health problems.

Some example implantable medical device (IMD) systems may be able to help such diseased hearts by providing electrical stimulation to the hearts. For example, such IMD systems may include electrodes implanted on or within the heart of the patient and may deliver electrical stimulation therapy to hearts through these electrodes. The delivered electrical stimulation therapy may replace or assist the intrinsically generated electrical signals in causing the contraction of the heart. One type of electrical stimulation therapy is termed cardiac resynchronization therapy (CRT). In general, CRT includes delivering electrical stimulation therapy to a heart, sometimes referred to as "pacing the heart" or delivering "pulses" or "pacing pulses," in order to ensure that all portions of the heart contract in a normal, synchronous manner.

In some examples, IMD systems for delivering CRT may include multiple electro-stimulation electrodes and may deliver electrical stimulation therapy via pairs (or sets) of electro-stimulation electrodes termed "vectors". Such example IMD systems typically use a selected vector of the available vectors for sensing cardiac electrical signals and/or for delivering electrical stimulation therapy. The specific physiology of a patient and the location of implanted electro-stimulation electrodes affect the suitability or desirability of each potential vector for use in sensing cardiac electrical signals and/or delivering electrical stimulation therapy, and because such parameters vary between patients, the suitability or desirability of each potential vector also often varies between patients.

FIG. 1 is a schematic view of an illustrative implantable medical system, which may be used, at least in part, to select one or more vectors for sensing cardiac electrical signals and/or delivering electrical stimulation therapy. FIG. 1 illustrates generally an example of a system 100 that can include an implantable medical device 101. Implantable medical device 101 can be coupled to one or more electro-stimulation electrodes, which can be carried by one or more implantable leads, such as implantable leads 110, 120, and 130. Implantable leads 110, 120, and 130 can be configured to receive or sense cardiac electrical signals from heart 115. In some cases, implantable medical device 101 can include a hermetically-sealed or similar housing 111. Housing 111 can include titanium or another biocompatible material, such as one or more other conductive materials.

In some instances, the electro-stimulation electrodes may be provided by a leadless cardiac pacemaker (LCP), which is in communication with other LCP's and/or with another implantable medical device 101. In at least some examples, the LCP(s) may generally comprise a pulse generator and a controller for controlling the pulse generator. The use of one or more LCPs may reduce or eliminate the need for one or more of the implantable leads 110, 120 and 130, as desired.

Generally, implantable medical device 101 may include an electro-stimulation or pulse generator device. Accordingly, in some examples, implantable medical device 101 may include one or more of a pacemaker, a defibrillator, an implantable monitor, a drug delivery device, a cardiac resynchronization therapy (CRT) device, a neural stimulation device, a baroreceptor stimulation device and/or one or more other implantable assemblies configured to monitor a person or configured to provide one or more electrical stimulation treatments to the person. Examples of such monitoring or treatment can include delivering electrical stimulation therapy to tissues such as cardiac tissue, or electrical monitoring of muscular or cardiac activity. In one example, implantable medical device 101 may include an external medical device, such as a pacing system analyzer, programmer recorder monitor, or other external medical device that can be used to configure a system of multipolar implantable leads. In some cases, implantable medical device 101 may include a subcutaneous Implantable Cardioverter-Defibrillator (S-ICD) and/or a subcutaneous pacemaker.

In the example of FIG. 1, implantable medical device 101 can be coupled to heart 115, or other body tissue, such as via electrode system 107, epicardial electrodes, or external (e.g., skin-patch) electrodes. In the system of FIG. 1, electrode system 107 includes at least one lead and at least one electro-stimulation electrode for each lead. FIG. 1 shows an example in which there are three implantable leads 110, 120, and 130. In the example of FIG. 1, implantable lead 110 can be configured for use in association with a left ventricle of heart 115. For example, implantable lead 110 can be sized and shaped to allow insertion into a coronary sinus and intravascular advancement such as to put at least one electro-stimulation electrode in association with the left ventricle of heart 115. Implantable lead 110 can be a multipolar lead, including a plurality of electro-stimulation electrodes and corresponding conductors. In an example, implantable lead 110 can include four discrete electro-stimulation electrodes, such as: tip electrode 112, first ring electrode 114, second ring electrode 116, and third ring electrode 118. In an example, electro-stimulation electrodes 114, 116, and 118 can be located near a distal portion of implantable lead 110. Each of electro-stimulation electrodes 114, 116, and 118 can be separated by electrically insulating material, thus electrically isolating the individual electro-stimulation electrodes. Each of the four left ventricular electro-stimulation electrodes 112, 114, 116, and 118 can correspond to a unique electrical conductor and can be individually addressable by sensing circuit 106 or electro-stimulation circuit 105 contained within implantable medical device 101.

In the example shown in FIG. 1, implantable lead 120 can include tip electrode 122, first coil electrode 124, and second coil electrode 126. As generally shown in FIG. 1, implantable lead 120 can, in one example, be inserted into the right atrium and right ventricle of heart 115 so that first coil electrode 124 is positioned in the right ventricle and second coil electrode 126 is positioned in the right atrium. Likewise, in the example of FIG. 1, implantable lead 130 can include tip electrode 132 and ring electrode 134. As generally shown in FIG. 1, implantable lead 130 can be configured for insertion into the right atrium of heart 115.

The physical illustration of implantable leads 110, 120, and 130 provided in FIG. 1 is an illustrative non-limiting example only. Other systems may include leads positioned differently with respect to heart 115. Additionally, other systems may have differing numbers of electro-stimulation electrodes, and the positioning of the electro-stimulation electrodes on the leads may differ. Other systems may also include more or less implantable leads. In a system that uses strictly LCPs, no leads may be required or even desired. In general, the systems and techniques of the present disclosure are amenable to any system including a plurality of electrodes that are configurable into a plurality of vectors, regardless of specific implant locations or electrode placement or numbers.

In one example, implantable medical device 101 can include a communication circuit 102, processor circuit 103, memory circuit 104, electro-stimulation circuit 105, and sensing circuit 106. Processor circuit 103 and memory circuit 104 can be used to control the operation of implantable medical device 101. For example, processor circuit 103 can be configured to detect a cardiac condition, such as by using the sensing circuit 106 or another physiological sensor, and to respond to the detected cardiac condition, such as by causing electro-stimulation circuit 105 to deliver electrical stimulation to heart 115 via one or more electrodes. Memory circuit 104 can include one or more parameters, such as for various pacing and sensing modes, test procedures or the like. Memory circuit 104 can be configured to store physiological data, such as data concerning the condition of heart 115. Memory circuit 104 can also be configured to store device data, such as data about a status of a test or a test result. In one example, implantable medical device 101 can use electro-stimulation circuit 105 or sensing circuit 106 to interface with electrode system 107. Electro-stimulation circuit 105 or sensing circuit 106 can be configured to generate an electro-stimulation signal to provide electrical stimulation therapy to heart 115, for example by using energy stored in a battery (not shown) that is stored within implantable medical device 101. Electro-stimulation circuit 105 or sensing circuit 106 can be electrically coupled to electrode system 107. For example, electrical stimulation can be transmitted from electro-stimulation circuit 105 to heart 115 via electrode system 107. Likewise, sensing circuit 106 may receive signals from electrode system 107. Communication circuit 102 can be configured to establish a data communication link between implantable medical device 101 and, for example, external assembly 140.

In some instances, implantable medical device 101 can be configured to perform vector assessments. For example, processor circuit 103 can cause electro-stimulation circuit 105 to deliver electrical stimulation via some or all of the vectors created by pairs of electro-stimulation electrodes connected to implantable leads 110, 120, and 130. Sensing circuit 106 may detect various parameters during the vector assessment and store the detected parameters in memory circuit 104. In some cases, processor circuit 103 may communicate the detected parameters to external assembly 140, via communication circuit 102. Additionally, external assembly 140 may be configured to receive detected parameters and display them with user interface 145.

Implantable medical device 101 can be configured to communicate (wired or wirelessly) via communication circuit 102 with a local or remote external device, such as external assembly 140. This can include using an RF, optical, acoustic, conductive, or other communication link. External assembly 140 can be a portion or part of a patient management system. In one example, external assembly 140 can communicate with one or more remote clients, such as web-based clients, or can be communicatively coupled to one or more servers, which can include medical and patient databases.

In some cases, external assembly 140 can include communication circuit 142, processor circuit 143, memory circuit 144, or user interface 145. In one example, communication circuit 142 can include inductive coils or radio frequency telemetry circuitry, and can be configured to communicate with implantable medical device 101. Processor circuit 143 and memory circuit 144 can be used to interpret information received from user interface 145, or can be used to determine when to use communication circuit 142 to exchange information with implantable medical device 101. In one example, processor circuit 143 and memory circuit 144 can be used to initiate a vector assessment controlled at least in part by external assembly 140 using electrode system 107. External assembly 140 can be used to perform vector assessments using electrode system 107 and can be configured to display results such as by user interface 145. In some cases, external assembly 140 is not used and it is implantable medical device 101 that is configured to perform vector assessments using electrode system 107

When used, external assembly 140 can be an adjunct (e.g., non-implantable) external assembly. In one example, external assembly 140 can include the features of implantable medical device 101 described above and below, such that external assembly 140 can be configured to be directly or indirectly coupled to the electrode system 107. For example, external assembly 140 can be configured to assess each of the potential vectors resulting from all the various combinations of electro-stimulation electrodes 112, 114, 116, 118, 122, 124, 126, 132, and 134. External assembly 140 may be able to perform an assessment by utilizing a power source (not shown) to deliver electrical stimulation therapy to electrode system 107. External assembly 140 may be equipped with one or more algorithms that automatically select one or more of the assessed vectors and configures implantable medical device 101 with the selected vectors. In other examples, a user, such as a physician or other medical professional, may view results of the assessment and provide selections of one or more vectors. These selected vectors may be communicated to implantable medical device 101 via communication circuit 142. By using external assembly 140 to perform vector assessments, implantable medical device 101 may conserve power.

User interface 145 of external assembly 140 can include, but is not limited to, a keyboard, a mouse, a light pen, a touch-screen, a display screen, a printer, or an audio speaker. In one example, user interface 145 can be configured as a full color, high definition graphical display, such as using an LCD computer monitor. In another example, user interface 145 can be configured for use as a monochromatic display, such as using a CRT monitor to display text. In some examples, user interface 145 can be configured to interactively present a graphical representation of vector assessments to a user. In other examples, user interface 145 can be configured to interactively present a text-based representation of vector assessments.

Figure 2:
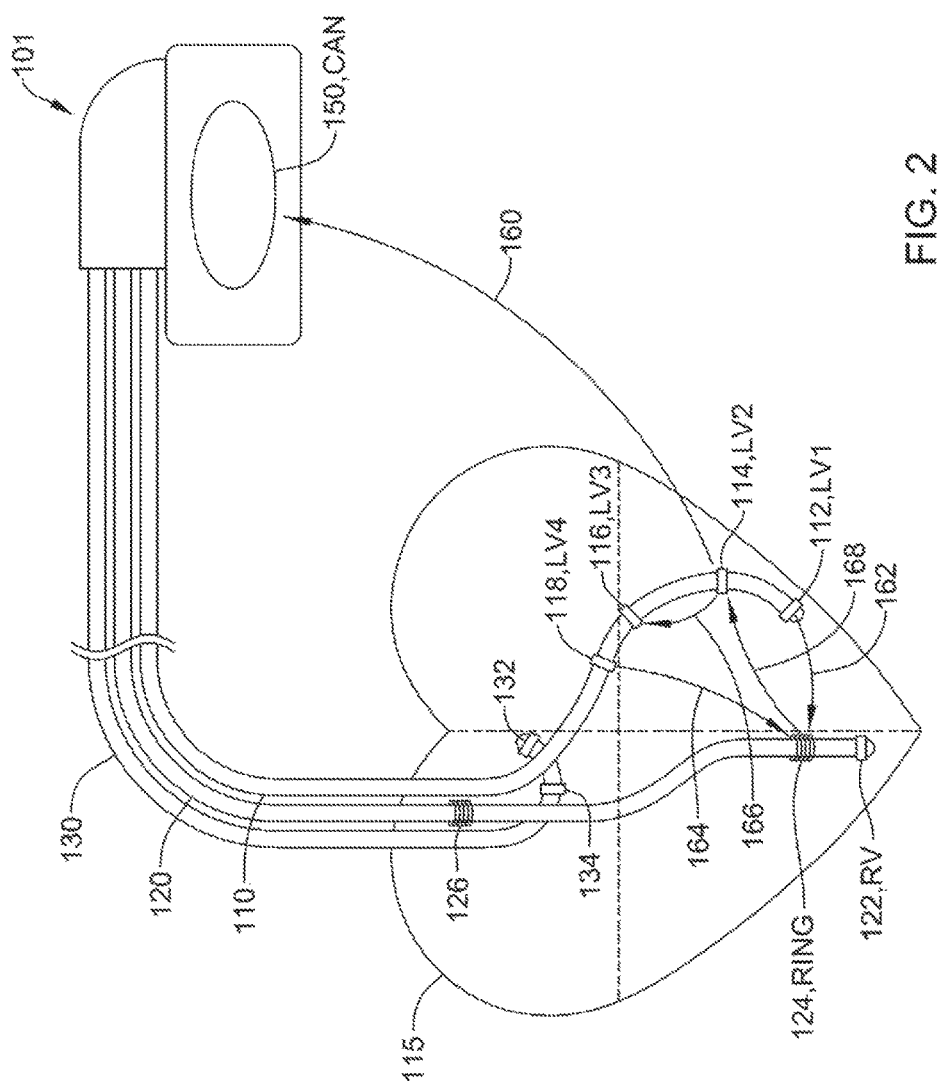
FIG. 2 is a schematic diagram of the implantable medical system of FIG. 1 showing various illustrative vectors.

FIG. 2 is a schematic diagram of the implantable medical system of FIG. 1 showing some exemplary vectors. As described with respect to FIG. 1, each pair of electro-stimulation electrodes of implantable medical device 101 may be considered a "vector". For each pair of electro-stimulation electrodes, a first one of the electro-stimulation electrodes is a cathode electrode and a second one of the electrodes is an anode electrode. In each of the illustrated example vectors, the arrow of each vector points to the anode electrode and the base of each arrow points to the cathode electrode. Although each vector is drawn as an arrow indicating a pathway, the vector only represents a general flow of electrical stimulation propagation when electrical stimulation is delivered via the particular vector. The exact pathway of electrical stimulation propagation will depend on many factors including physiological and physical system factors.

In some examples, implantable medical device 101 further includes a "can" electrode 150, as shown in FIG. 2. FIG. 2 further illustrates example vectors 160, 162, 164, 166, and 168. In FIG. 2, electro-stimulation electrodes 112, 114, 116, 118, 122, 124, and 150 are also labeled as LV1, LV2, LV3, LV4, RV, RING, and CAN, respectively, which are terms sometimes used in the art. Vector 160 represents the pair of the CAN electrode and the LV2 electrode, where the CAN electrode is an anode electrode and the LV2 electrode is a cathode electrode. The other vectors 162, 164, 166, and 168 all represent examples of vectors of implantable medical device 101. It should be understood that any combination of electro-stimulation electrodes may represent a unique vector. Additionally, each pair of electro-stimulation electrodes can actually produce two vectors because either of the pair of electro-stimulation electrodes can be the cathode electrode or the anode electrode. Table 1, below, lists all of the possible vectors of implantable medical device 101 comprising the RING, LV1, LV2, LV3, LV4, and CAN electrodes. The totality of possible vectors of implantable medical device 101 would further comprise combinations including electrodes 126, 132, 134, and RV. However, it should be understood that in other implantable medical device systems, particularly those with differing amounts of electrodes, the number of vectors of the system may be different. The example techniques described herein may be applicable to any such system including multiple electrodes.

TABLE 1

| Vector | Electrode Combination (Cathode Electrode → Anode Electrode) |
| --- | --- |
| Vector 1 (164) | LV1 → RING |
| Vector 2 | LV1 → LV4 |
| Vector 3 | LV1 → LV3 |
| Vector 4 | LV1 → LV2 |
| Vector 5 | LV1 → CAN |
| Vector 6 (184) | LV2 → RING |
| Vector 7 | LV2 → LV4 |
| Vector 8 | LV2 → LV3 |
| Vector 9 | LV2 → LV1 |
| Vector 10 (160) | LV2 → CAN |
| Vector 11 (182) | LV3 → RING |
| Vector 12 | LV3 → LV4 |
| Vector 13 (166) | LV3 → LV2 |
| Vector 14 | LV3 → LV1 |
| Vector 15 | LV3 → CAN |
| Vector 16 (162) | LV4 → RING |
| Vector 17 | LV4 → LV1 |
| Vector 18 | LV4 → LV2 |
| Vector 19 | LV4 → LV3 |
| Vector 20 | LV4 → CAN |
| Vector 21 | RING → LV1 |
| Vector 22 | RING → LV2 |
| Vector 23 (168) | RING → LV3 |
| Vector 24 | RING → LV4 |
| Vector 25 | RING → CAN |
| Vector 26 | CAN → RING |
| Vector 27 | CAN → LV1 |
| Vector 28 | CAN → LV2 |
| Vector 29 | CAN → LV3 |
| Vector 30 | CAN → LV4 |

Although the examples described below with respect to FIGS. 3-13 are described with respect to implantable medical device 101, it should be understood that the disclosed techniques may be applicable to any suitable device or system capable of delivering electrical stimulation therapy, including external assembly 140 coupled to implanted leads having a number of electro-stimulation electrodes.

Figure 3:
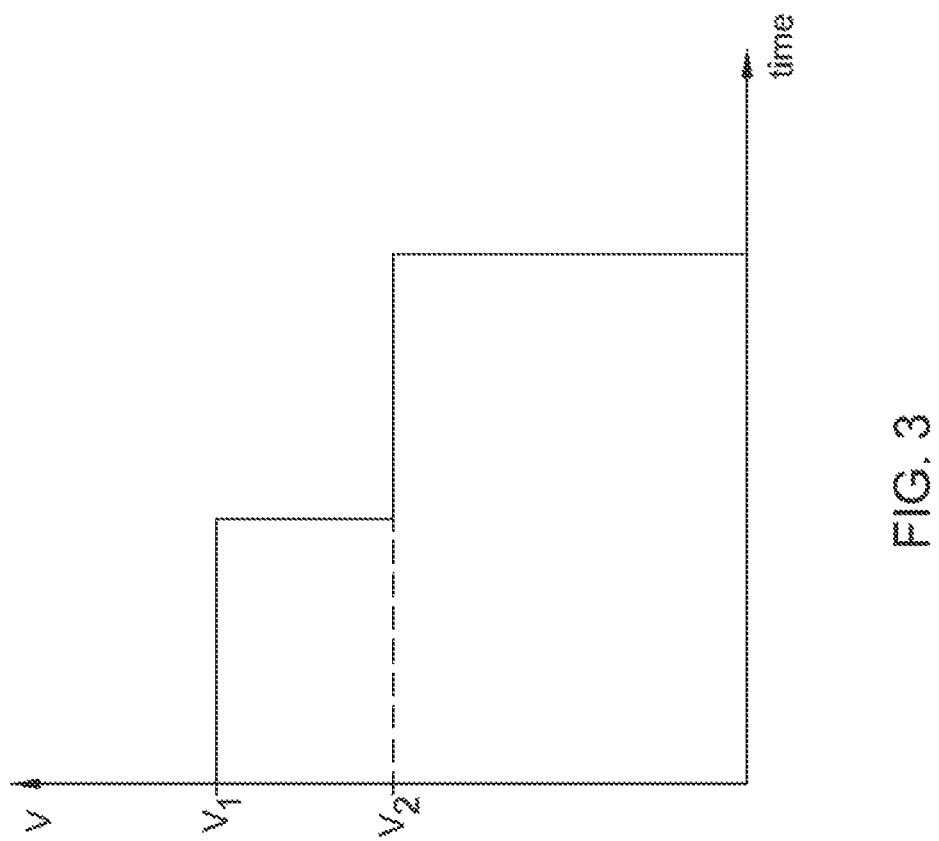
FIG. 3 is a graph that represents electrical stimulation levels that may be delivered to a heart of a patient by the implantable medical system of FIG. 1.

FIG. 3 shows a graph of voltage versus time, and represents one example operation of a medical device or system that may be used to assist in determining a capture threshold for a vector or in selecting one or more vectors for use in delivering electrical stimulation therapy. In the example of FIG. 3, implantable medical device 101 may be implanted within a heart and may deliver electrical stimulation therapy, for example pacing pulses, to heart 115. Device 101 may deliver pacing pulses to each vector of a first set of vectors resulting from electro-stimulation electrodes connected to leads 110, 120, and 130 implanted within heart 115. In some examples, the first set of vectors comprises all vectors of device 101 resulting from each possible unique pairing of the electro-stimulation electrodes of device 101. In other examples, the first set of vectors may be a sub-set of all the vectors (i.e. less than all of the vectors), which in this context, may range from a single vector to one less than all of the vectors. In at least some examples, device 101 may operate to determine one or more parameters for each vector, such as an impedance parameter, a capture threshold parameter, a delay parameter, and/or a phrenic nerve stimulation value. Device 101 may obtain one or more of these parameters by delivering electrical stimulation to heart 115 via each vector and measuring each parameter. Device 101 may be configured to automatically select one or more vectors to include in the first set of vectors based on such determined parameters. In other examples, device 101 may be configured to receive input from a user including selection of which vectors to include in the first set of vectors, such as through external assembly 140. In still other examples, device 101 may be configured to operate to determine one or more parameters and/or select which vectors to include in the first set of vectors according to the techniques detailed in provisional patent application Ser. No. 61/917,836, filed Dec. 18, 2013, and entitled "SYSTEMS AND METHODS FOR FACILITATING SELECTING OF ONE OR MORE VECTORS IN A MEDICAL DEVICE", which is incorporated herein by reference in its entirety.

Device 101 may then deliver one or more pacing pulses via one of the vectors in the first set of vectors at a first voltage level $V_1$. Device 101 may then determine and record whether the one or more delivered pacing pulses captured heart 115. Device 101 may determine whether the pacing pulse or pulses captured the heart 115 by sensing for cardiac electrical signals after delivering the pacing pulse or pulses. If device 101 senses cardiac electrical signals, or a particular pattern of cardiac electrical signals that correspond to capture, device 101 may determine that the pacing pulse or pulses captured heart 115. Device 101 may then deliver one or more pacing pulses at the first voltage level $V_1$ via another of the vectors in the first set of vectors and determine whether the delivered pacing pulse or pulses captured heart 115. In a similar manner, device 101 may deliver one or more pacing pulses and determine whether the delivered pulse or pulses captured heart 115 for each vector in the first set of vectors.

After determining whether the delivered pacing pulse or pulses captured heart 115 at the first voltage level $V_1$ for each vector in the first set of vectors, device 101 may then identify those vectors for which the pacing pulse or pulses did capture the heart 115 and group those vectors into a second set of vectors. Device 101 may then deliver one or more pacing pulses at a second, lower voltage level, $V_2$, to one of the vectors in the second set of vectors. Device 101 can determine whether the delivered pacing pulse or pulses at the second voltage level $V_2$ captured the heart 115 for the vector. Device 101 may repeat this process for each vector in the second set of vectors.

In other examples, device 101 may deliver one or more pacing pulses at the first voltage level $V_1$ and, in some instances, the second voltage level $V_2$, via a first vector of the first set of vectors before delivering pacing pulses via any other of the vectors of the first set of vectors. For example, device 101 may deliver one or more pacing pulses at the first voltage level $V_1$ via a first vector of the first set of vectors. Device 101 may then determine whether the one or more delivered pacing pulses captured the heart 115. If the one or more pacing pulses did capture the heart, device 101 may then deliver one or more pacing pulses via the first vector at the second voltage level $V_2$. Again, device 101 may determine whether the delivered one or more pacing pulses at the second voltage level $V_2$ captured heart 115. If device 101 determined that the one or more delivered pacing pulses at the first voltage level $V_1$ did not capture the heart 115, device 101 may not deliver one or more pacing pulses via the first vector at the second voltage level $V_2$. Device 101 may record whether the one or more pacing pulses at the first voltage level $V_1$ and/or the second voltage level $V_2$ captured the heart 115. Device 101 may then repeat a similar process for each of the other vectors in the first set of vectors.

In some examples, if none of the vectors at the first voltage level $V_1$ captured the heart 115, device 101 may increase the voltage value of the first voltage level $V_1$ and begin the process again. For example, device 101 may start again delivering pacing pulses at a new, higher first voltage level $V_1$ using the vectors in the first set of vectors in a manner according to any of the examples described above.

In some cases, the first voltage level V1 may be a predetermined value stored in memory 104 and/or memory 144. In some cases, the first voltage V1 may be input by a user, such as through user interface 145. In some cases, the first voltage level V1 may be set at a level that is expected to be above the capture threshold for all of the vectors in the first set of vectors (e.g. 7 volts). In other instances, the first voltage level V1 may be set to a level that is deemed by the user to be an acceptable voltage level for subsequent long term pacing (e.g. 3 volts), and the system may determine which of the vectors of the first set of vectors do not capture the heart at that voltage level and may automatically eliminate those vectors from the second set of vectors.

Figure 4:
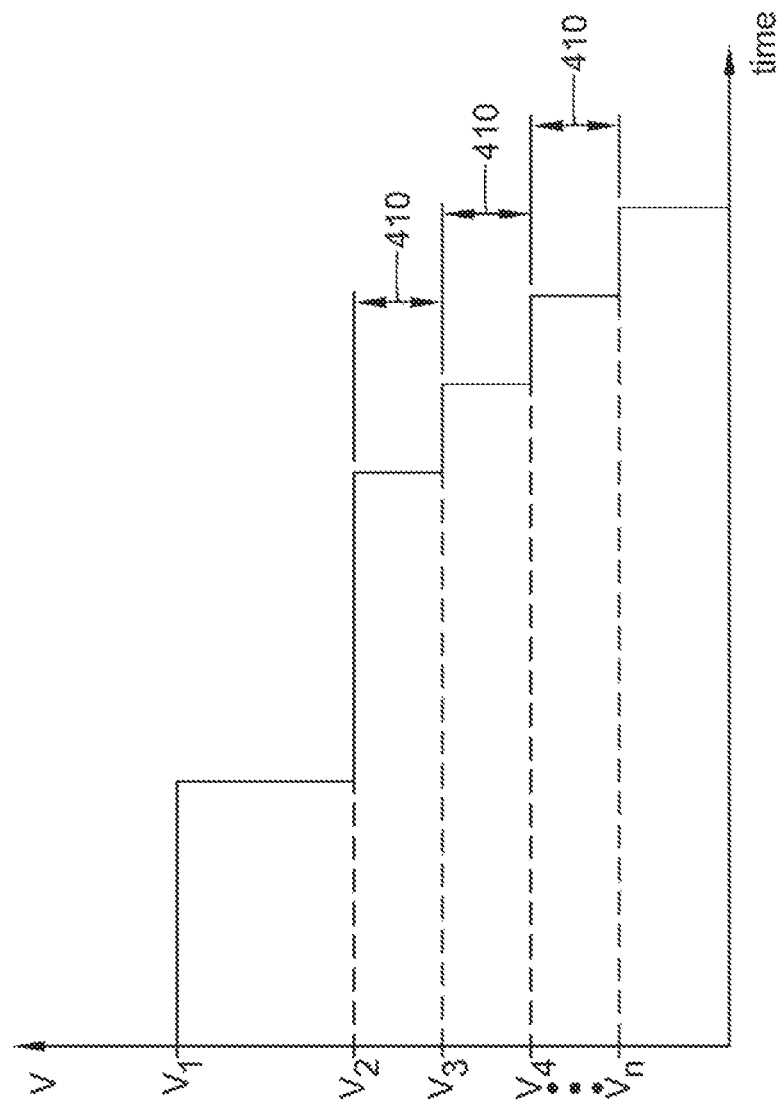
FIG. 4 is a graph that represents electrical stimulation levels that may be delivered to a heart of a patient by the implantable medical system of FIG. 1.

FIG. 4 describes additional examples where device 101 may determine a capture threshold for one or more of the vectors. In such examples, for each of the vectors via which device 101 delivered pacing pulses at the second voltage level $V_2$ and determined that the pulses captured heart 115, device 101 may subsequently deliver pacing pulses at successively lower voltage values until determining that the delivered pacing pulse or pulses failed to capture the heart 115. For example, device 101 may deliver one or more pacing pulses via a vector at a third voltage level $V_3$ that is less than the second voltage level $V_2$. If device 101 determines that the delivered one or more pacing pulses captured the heart 115, device 101 may then deliver one or more pacing pulses at a fourth voltage level $V_4$ that is less than the third voltage level $V_3$. Device 101 may then determine whether the delivered pacing pulse or pulses captured heart 115. Device 101 may repeat this process until determining that the one or more delivered pacing pulses failed to capture the heart 115 at a voltage level $V_n$ for the vector and then record the lowest voltage level of delivered pacing pulses that captured the heart 115 as the capture threshold for that vector. For instance, in the above example, if the delivered pulse or pulses at the fourth voltage level $V_4$ via a vector failed to capture the heart 115, device 101 may record the third voltage level $V_3$ as the capture threshold for that vector.

In some examples, the first and second voltage levels, $V_1$ and $V_2$, may be configurable by a user. For example, a user may input values into an external device, for example external assembly 140, and the external device may communicate the values to device 101. Device 101 may then configure the first and second voltage levels, $V_1$ and $V_2$, according to the input values. In other examples the first and second voltage levels, $V_1$ and $V_2$, may be predetermined values and stored in memory circuit 104 of device 101. Some example predetermined values for the first voltage level $V_1$ are 5 volts, 4.5 volts, 3.5 volts, 2 volts, 1.5 volts, and 1 volt, or any other suitable voltage value. Some example values for the second voltage level $V_2$ are 4 volts, 3.5 volts, 2.5 volts, 2 volts, 1.5 volts, and 1 volt, or any other suitable voltage value.

In examples where device 101 determines a capture threshold, device 101 may be configured to successively step down voltage levels by a predetermined step down value 410. For instance, in the example above, device 101 may be configured to use a third voltage level $V_3$ that is a step value 410 less than the second voltage level $V_2$. Accordingly, the fourth voltage level $V_4$ may also be step value 410 less than the third voltage level $V_3$. In some examples, step value 410 may also be configurable by a user. In other examples, step value 410 may be predetermined and stored in memory circuit 104. In at least some examples, step value 410 is less than the difference between the first and second voltage levels, $V_1$ and $V_2$.

In examples where the first and second voltage levels, $V_1$ and $V_2$, are configurable by a user, each of the first and second voltage levels, $V_1$ and $V_2$, may have maximum allowable values. Some example maximum allowable values for the voltage levels are 7 volts, 6 volts, and 5 volts, or any other suitable voltage value. If a user inputs a value above the maximum allowable value, device 101 may set the voltage levels at the maximum allowable value, or the user will be prevented from entering a value above the maximum allowable value. In some examples, step value 410 may also have a maximum allowable value. For example, step value 410 may have a maximum allowable value of 0.5 volts, 0.4 volts, 0.3 volts, or any other suitable voltage value. In some cases, the first and second voltage levels, and the step value 410, may have minimum allowed values.

Figure 5:
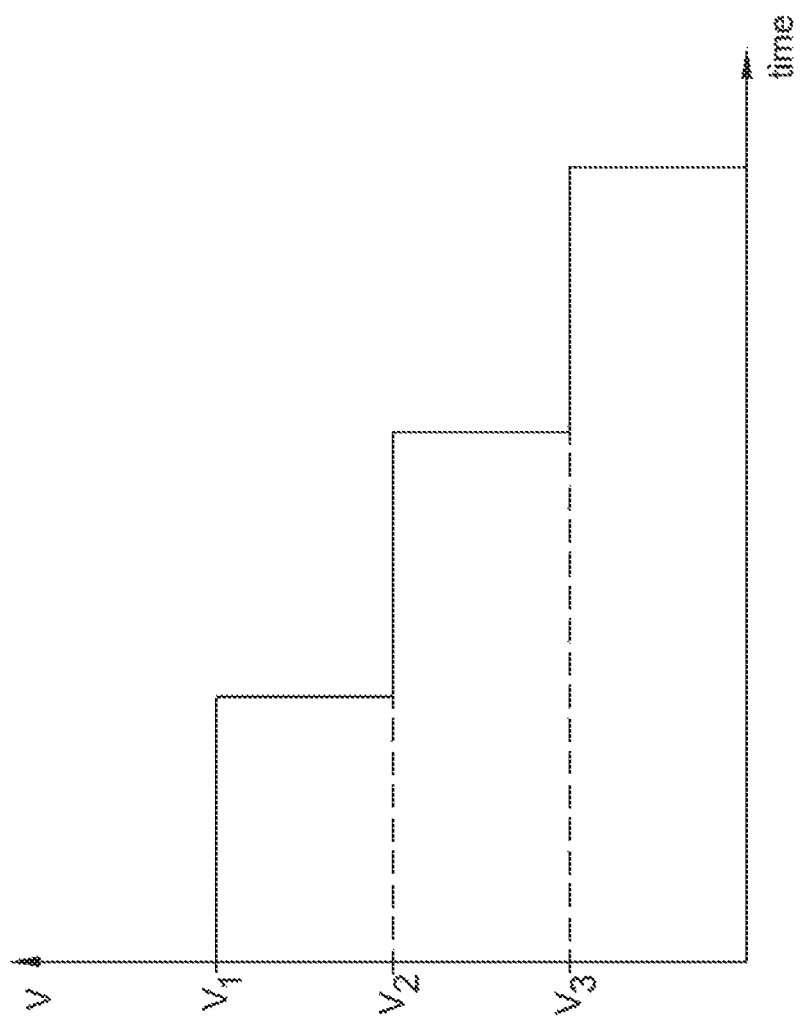
FIG. 5 is a graph that represents electrical stimulation levels that may be delivered to a heart of a patient by the implantable medical system of FIG. 1.

FIG. 5 depicts a graph illustrating additional example operations of a medical device or system that may be used to assist in determining a capture threshold for a vector or in selecting one or more vectors for use in delivering electrical stimulation therapy. For example, device 101 may additionally test a set of vectors at a third voltage level $V_3$, in addition to first testing a set of vectors at first and second voltage levels $V_1$ and $V_2$. For example, after delivering a pacing pulse or pulses via the vectors in the second set of vectors, as described above with respect to FIGS. 3 and 4, device 101 may group those vectors for which device 101 determined that the delivered pacing pulse or pulses at the second voltage level $V_2$ captured heart 115 into a third set of vectors. Device 101 may then deliver a pacing pulse or pulses at the third voltage level $V_3$ via a first vector of the third set of vectors and determine whether the delivered pacing pulse or pulses captured heart 115. Device 101 may repeat this process for each of the vectors in the third set of vector and record the results.

In some examples device 101 may deliver pacing pulses at the first, second, and/or third voltage levels, $V_1$, $V_2$, and $V_3$, to a vector of the first set of vectors before delivering a pacing pulse or pulses to other vectors of the first set of vectors. For example, device 101 may deliver a pacing pulse or pulses at the first voltage level $V_1$ and determine whether the delivered pacing pulses captured heart 115. Device 101 then may repeat this process at the second, and if necessary the third voltage level for the vector. If device 101 determines that the delivered pacing pulse or pulses at any of the voltage levels failed to capture the heart 115, device 101 may cease delivering pacing pulses via that vector and switch to another of the vectors of the first set of vectors. Device 101 may then begin delivering pacing pulses via the next vector of the first set of vectors. Device 101 may repeat this process for each of the vectors in the first set of vectors.

Figure 6:
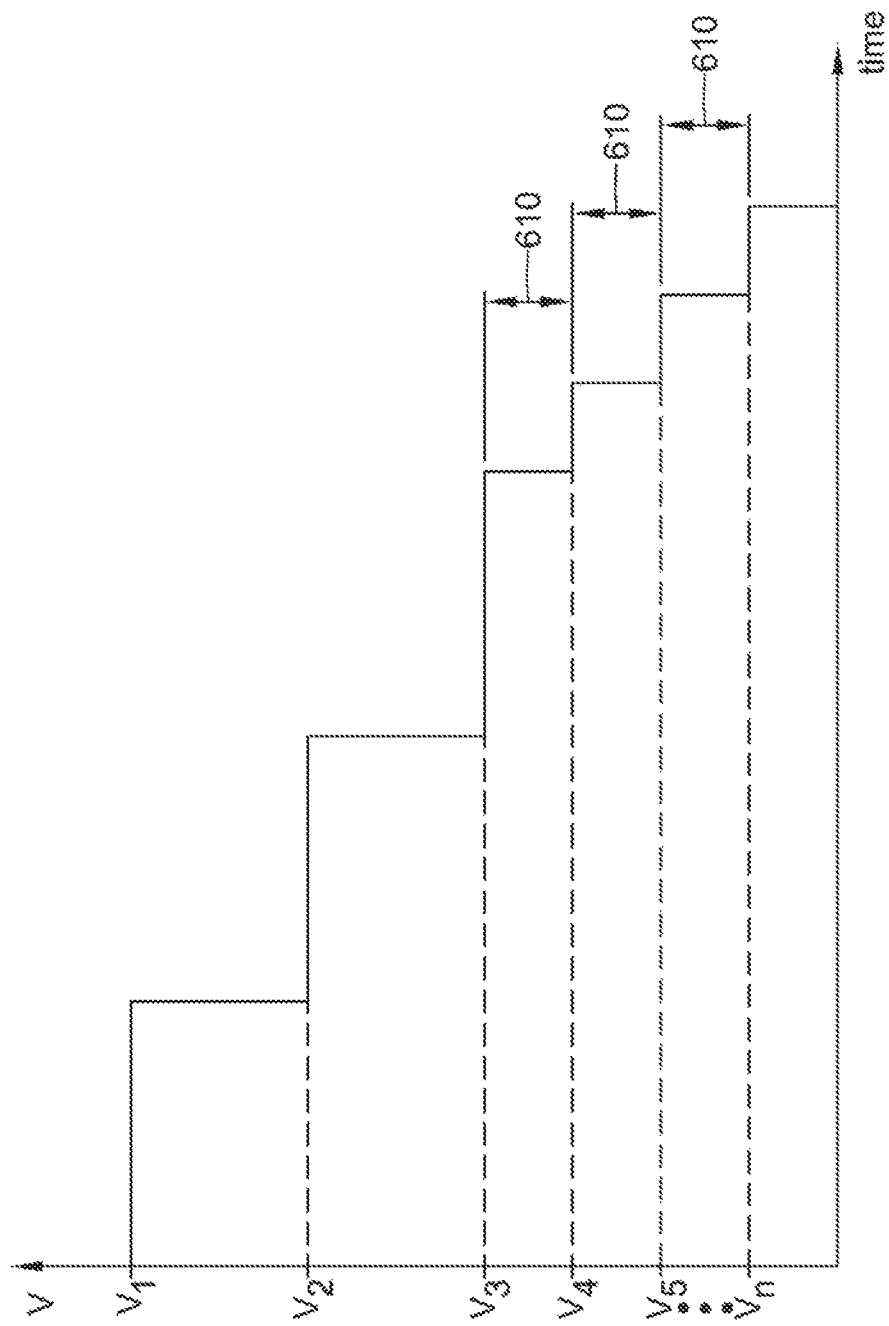
FIG. 6 is a graph that represents electrical stimulation levels that may be delivered to a heart of a patient by the implantable medical system of FIG. 1.

FIG. 6 depicts a graph illustrating another example operation of device 101. In the example of FIG. 6, device 101 may perform any of the techniques described above with respect to FIG. 5 and may additionally determine a capture threshold for one or more of the vectors. For example, for each of the vectors via which device 101 delivered pacing pulses at the third voltage level $V_3$ and determined that the pulses captured heart 115, device 101 may subsequently deliver pacing pulses at successively lower voltage values until determining that the delivered pacing pulse or pulses failed to capture the heart 115. In such examples, device 101 may deliver one or more pacing pulses at a fourth voltage level, $V_4$, that is less than the third voltage level $V_3$. If device 101 determines that the one or more pacing pulses delivered at the fourth voltage level $V_4$ captured the heart 115, device 101 may then deliver one or more pacing pulses at a fifth voltage level, $V_5$, that is less than the fourth voltage level $V_4$. Device 101 then determines whether the delivered pacing pulse or pulses captured the heart 115. Device 101 may repeat this process until determining that the one or more delivered pacing pulses failed to capture the heart 115 at a voltage level $V_n$ and then record the lowest voltage level of delivered pacing pulses that captured the heart 115 as the capture threshold. For instance, in the above example, if the delivered pulse or pulses at the fourth voltage level $V_4$ via a vector failed to capture the heart 115, device 101 may record the third voltage level $V_3$ as the capture threshold for the vector.

In the examples of FIGS. 5 and 6, the various voltage levels, $V_1$, $V_2$, and $V_3$ may be configurable by a user. For example, a user may input values in an external device, for example external assembly 140, and the external device communicates the values to device 101. Device 101 may then configure the first, second, and third voltage levels, $V_1$, $V_2$, and $V_3$, according to the input values. In other examples, the first, second, and third voltage levels, $V_1$, $V_2$, and $V_3$, may be predetermined values and stored in memory circuit 104 of device 101. Some example predetermined values for the first voltage level $V_1$ are 5 volts, 4.5 volts, 3.5 volts, 2 volts, 1.5 volts, and 1 volt, or any other suitable voltage value. Some example values for the second and third voltage levels, $V_2$ and $V_3$, are 4 volts, 3.5 volts, 2.5 volts, 2 volts, 1.5 volts, and 1 volt, or any other suitable voltage value. In some examples, device 101 may be configured to successively step down voltage levels by a predetermined step value 610. For instance, in the example above, device 101 may be configured to use a fourth voltage level $V_4$ that is step value 610 less than the third voltage level $V_3$. Accordingly, any subsequent voltage levels may also be step value 610 less than each previous voltage level of delivered pacing pulses. In some examples, step value 10 may be configurable by a user. In other examples, step value 610 may be predetermined and stored in memory circuit 104. In at least some examples, step value 610 is less than the difference between the first and second voltage levels, $V_1$ and $V_2$.

In examples where the first, second, and third voltage levels, $V_1$, $V_2$, and $V_3$, are configurable by a user, each of the first, second, and third voltage levels, $V_1$, $V_2$, and $V_3$, may have maximum allowable values. Some example maximum values for the voltage levels are 7 volts, 6 volts, and 5 volts, or any other suitable voltage value. If a user inputs a value above the maximum allowable value, device 101 may set the voltage levels with the maximum allowable value, or the user will be prevented from entering a value above the maximum allowable value. In some examples, step value 610 may also have a maximum allowable value. For example, step value 610 may have a maximum allowable value of 0.5 volts, 0.4 volts, 0.3 volts, or any other suitable voltage value. In some cases, the first and second voltage levels, and the step value 410, may have minimum allowed values.

Figure 7:
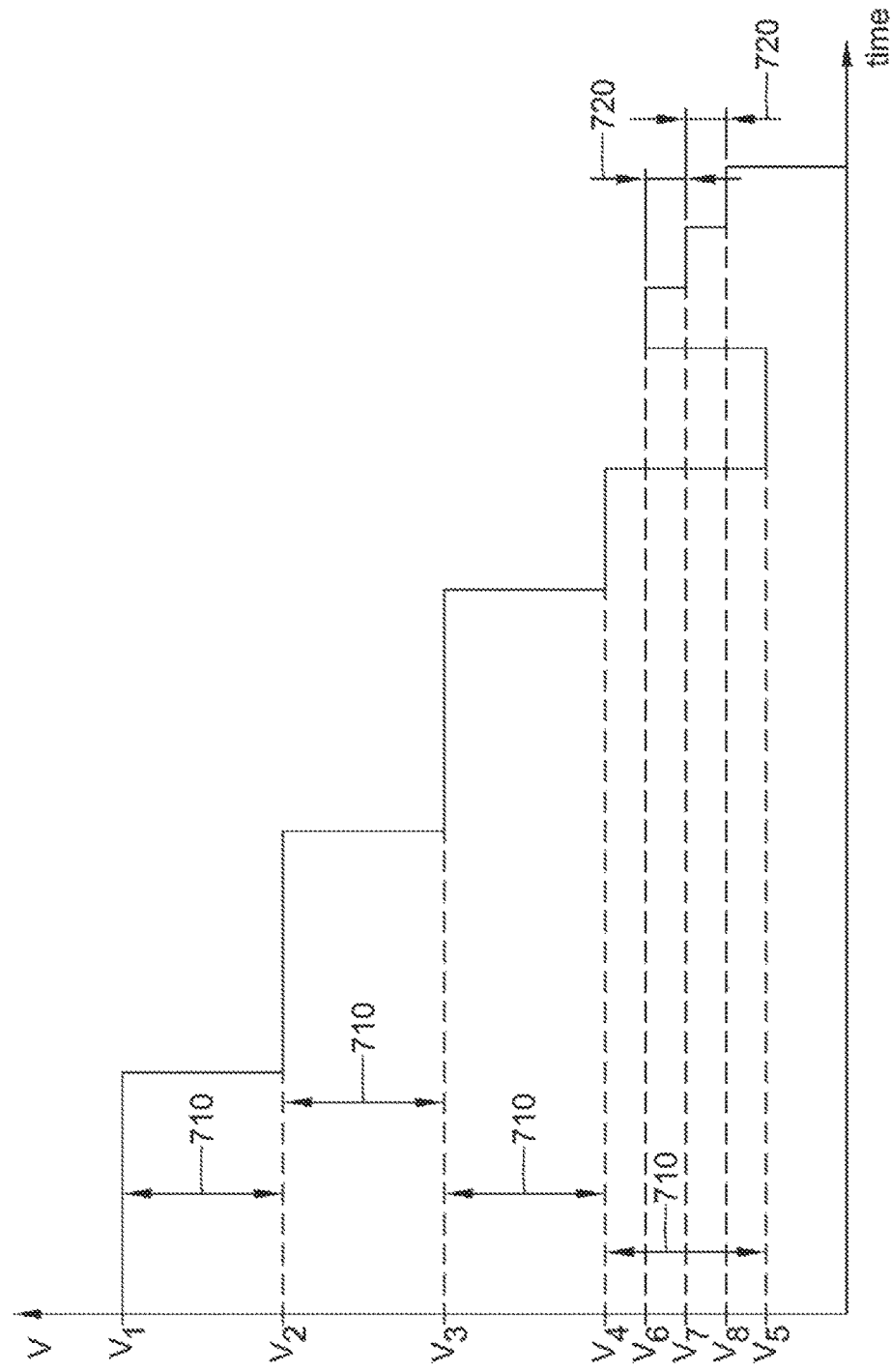
FIG. 7 is a graph that represents electrical stimulation levels that may be delivered to a heart of a patient by the implantable medical system of FIG. 1.

FIG. 7 depicts a graph illustrating another example operation of device 101 in determining a capture threshold for a vector or assisting in selecting one or more vectors for use in delivering electrical stimulation therapy. In the example of FIG. 7, device 101 may deliver a pacing pulse or pulses at a first voltage level $V_1$ for a first vector in a set of vectors. As with the examples described in conjunction with FIG. 3, the set of vectors may be selected by device 101 or a user, sometimes based on one or more parameters of the vectors. After delivering the pacing pulse or pulses at the first voltage level $V_1$, device 101 may determine whether the delivered pacing pulse or pulses captured the heart 115. If device 101 determines that the delivered pacing pulse or pulses captured the heart 115, device 101 may step down the voltage by first step value 710, resulting in a new, second voltage level, $V_2$. Device 101 may then deliver one or more pacing pulses to the heart via the vector at the second voltage level $V_2$ and determine whether the delivered pacing pulse or pulses captured the heart 115.

Device 101 may repeat this process of stepping down the voltage level to a new, lower voltage level until device 101 determines that the delivered pacing pulse or pulses failed to capture the heart 115. In the example of FIG. 7, device 101 may deliver one or more pacing pulses at voltage levels $V_3$, $V_4$, and $V_5$, and determine that only at voltage level $V_5$ does the delivered pacing pulse or pulses fail to capture the heart 115. Upon determining that the pacing pulse or pulses failed to capture the heart 115, for example voltage level $V_5$ in the example of FIG. 7, device 101 may then raise the voltage level. In some examples, device 101 may raise the voltage level to a level that is a second step value 720 less than the lowest voltage level at which device 101 determined that a delivered pacing pulse or pulses captured the heart 115, which in the present example was voltage level $V_4$. The new voltage level is labeled $V_6$ in FIG. 7. Device 101 may then deliver one or more pacing pulses at voltage value $V_6$ and determine whether the pacing pulse or pulses captured the heart 115. If device 101 determines that the delivered pacing pulse or pulses captured the heart 115, device 101 may again decrease the voltage level by second step value 720, resulting in voltage level $V_7$. As above, device 101 may continue this process until determining that a delivered pacing pulse or pulses at a current voltage level fails to capture the heart 115.

In some cases, the delivered pacing pulse or pulses at voltage value $V_6$ will also fail to capture heart 115. In such cases, as before, device 101 may record the lowest voltage at which capture was detected as the capture threshold. For instance, in the above example, device 101 would record voltage value $V_4$ as the capture threshold, as voltage value $V_4$ was the lowest voltage level at which device 101 detected that delivered pacing pulse or pulses captured heart 115.

Upon determining that the delivered pacing pulse or pulses at the current voltage level failed to capture the heart 115, device 101 may record the lowest voltage level at which the delivered pacing pulse or pulses captured heart 115 as the capture threshold for the vector. For instance, in FIG. 7, after determining that the delivered pacing pulse or pulses at voltage level $V_7$ captured heart 115, device 101 may deliver one or more pacing pulses at voltage level $V_8$. In the example, device 101 may determine that the delivered pacing pulse or pulses at voltage level $V_8$ failed to capture the heart 115. Accordingly, device 101 may record voltage level $V_7$ as the capture threshold for the given vector.

In some examples, before delivering one or more pacing pulses at voltage level $V_6$, device 101 may raise the voltage level back to the previous voltage level where a delivered pacing pulse or pulses captured heart 115, such as voltage level $V_4$ in FIG. 7. Device 101 may then deliver one or more pacing pulses at this previous voltage level, voltage level $V_4$ in the example of FIG. 7, and confirm that the delivered pacing pulses or pulses captured the heart 115. Upon confirming that the delivered pacing pulse or pulses captured the heart 115, device 101 may then step down the voltage level by second step value 720, resulting in a new, lower voltage value $V_6$. Device 101 may then proceed according to the process described above.

Figure 8:
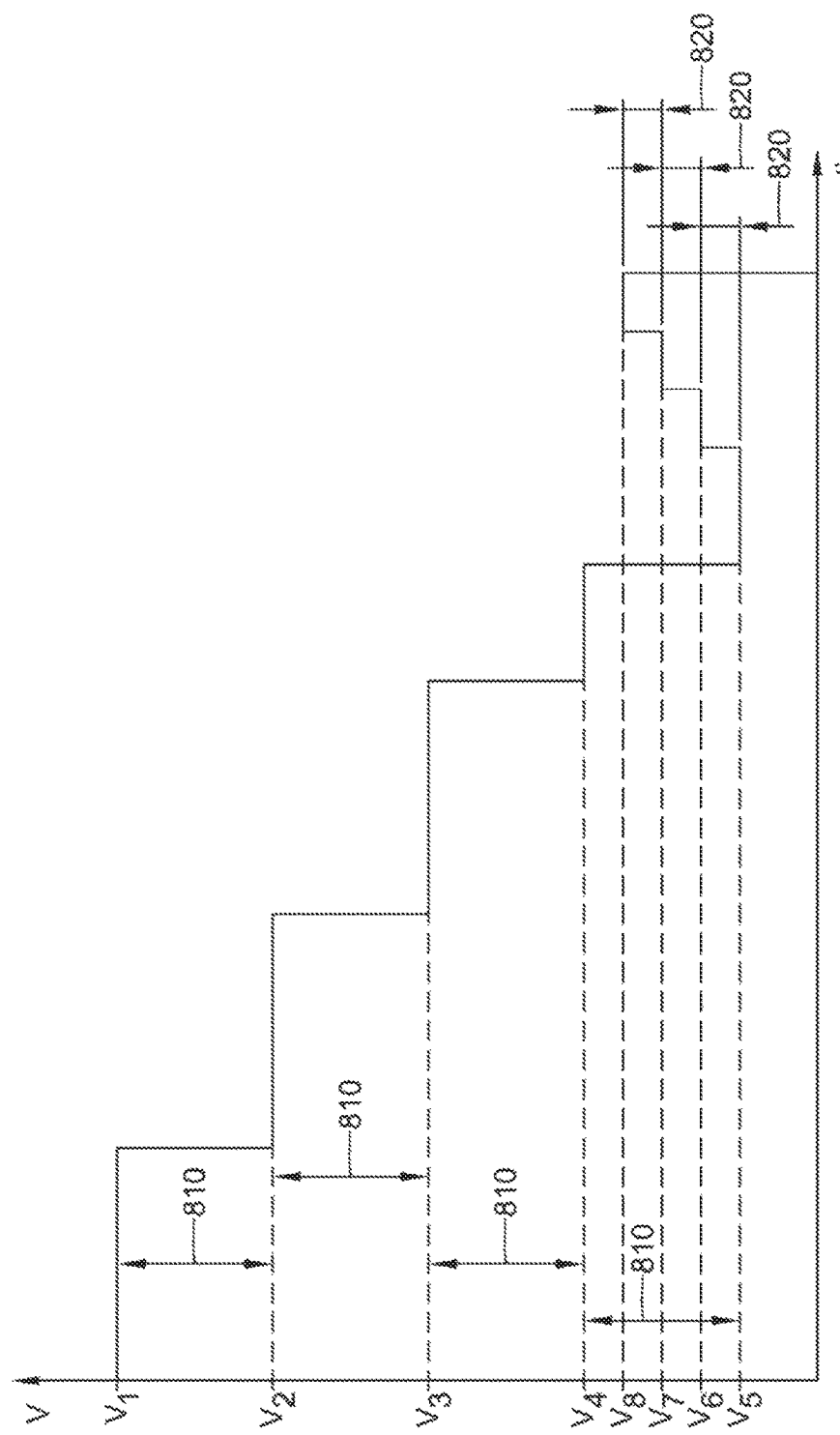
FIG. 8 is a graph that represents electrical stimulation levels that may be delivered to a heart of a patient by the implantable medical system of FIG. 1.

FIG. 8 depicts a graph illustrating another example operation of device 101 in determining a capture threshold for a vector or assisting in selecting one or more vectors for use in delivering electrical stimulation therapy. In the example of FIG. 8, device 101 may deliver a pacing pulse or pulses in a manner similar to that described with respect to FIG. 7. For example, device 101 may deliver one or more pacing pulses at a first voltage level $V_1$ and determine whether the delivered pacing pulse or pulses captured heart 115. Upon determining that the delivered pacing pulses captured heart 115, device 101 may decrease the voltage level by first step value 810, which results in a second, lower voltage level $V_2$. Device 101 may then deliver one or more pacing pulses at the second voltage level $V_2$ and determine whether the delivered pacing pulses captured the heart 115. Device 101 may repeat this process until device 101 determines that the delivered pacing pulse or pulses for a current voltage level failed to capture the heart 115. In the example of FIG. 8, device 101 determines that the pacing pulse or pulses delivered at the fifth voltage level $V_5$ failed to capture the heart 115.

After determining that the delivered pacing pulse or pulses failed to capture the heart 115, device 101 may raise the voltage level. For example, device 101 may raise the voltage level by second step value 820. In the example of FIG. 8, this may result in a new voltage level, $V_6$ which is higher than voltage level $V_5$ by a second predetermined amount 820. Device 101 may then determine whether one or more delivered pacing pulses at voltage level $V_6$ captured the heart 115. Device 101 may continue this process of increasing the voltage level by second step value 820 until device 101 determines that one or more pacing pulses delivered at a voltage level captures that heart 115. Device 101 may then determine that this voltage level at which the delivered pacing pulses captured the heart 115 is the capture threshold for the vector. For instance, in FIG. 8, device 101 may determine that a delivered pacing pulse or pulses at voltage levels $V_6$ and $V_7$ failed to capture the heart 115, but that delivering one or more pacing pulses at voltage level $V_8$ captured the heart 115. Accordingly, device 101 may record that voltage $V_8$ as the capture threshold for the vector.

Device 101 may include one or more safety features. In some examples, device 101 may additionally sense for intrinsic cardiac activity. Device 101 may further monitor a predetermined safety period which resets after each delivered pacing pulse that captures the heart 115, and may sense intrinsic cardiac activity indicating a contraction of heart 115. Upon the expiration of the predetermined safety period, device 101 may be configured to deliver one or more pacing pulses via a specific vector at a specific voltage level. In some examples, the vector and voltage level are predetermined. In other examples, the vector and voltage level may be determined by device 101. For example, device 101 may select a vector and voltage level to help ensure that the delivered pacing pulse or pulses capture the heart 115, such as by selecting a vector and voltage level at which previously delivered pacing pulses had captured the heart 115. Such a safety feature may help ensure that heart 115 contracts at least once every predetermined safety period. This may help ensure that the contraction rate of heart 115 does not get too low during the capture threshold testing. Such a safety feature may be particularly useful in examples where device 101 delivers a pacing pulse or pacing pulses at successively higher voltage levels after determining a delivered pacing pulse or pulses failed to capture the heart 115.

In some instances, the first and second step values, e.g. step values 710 and 720 as described with respect to FIG. 7 or step values 810 and 820 as described with respect to FIG. 8, may be configurable by a user. For example, a user may input values into system 100, such as through an interface at an external device, such as external assembly 140. External device 140 may then communicate the input values to device 101, and device 101 may configure the first and second step values with the input values. In other examples, the first and second step values may be predetermined values that device 101 stores in memory circuit 104. In some instances, the first and second step values may have maximum allowable values. Some example maximum allowable values for a first step value include 0.5 volts, 0.4 volts, and 0.3 volts, or any other suitable voltage value. Some example maximum allowable values for a second step value include 0.25 volts, 0.2 volts, and 0.15 volts, or any other suitable voltage value. In some instances, the first and second step values may have minimum allowable values.

It should be understood that the above described techniques are only illustrative examples. Other examples are contemplated that may differ from those described above yet are still within the scope of this disclosure. For instance, in the above examples of FIGS. 3-8, device 101 has been described as automatically determining whether delivered electrical stimulation has captured the heart. However, in other examples, a user may determine whether the delivered electrical stimulation has captured the heart. In such examples, a user may view cardiac electrical signals on a display device that have been sensed by device 101 or another device. Based on the displayed cardiac electrical signals, a user may enter input, such as through user interface 145, indicating whether the delivered electrical stimulation captured the heart. Other differences from the specific disclosed examples also fall within the scope of this disclosure.

Figure 9:
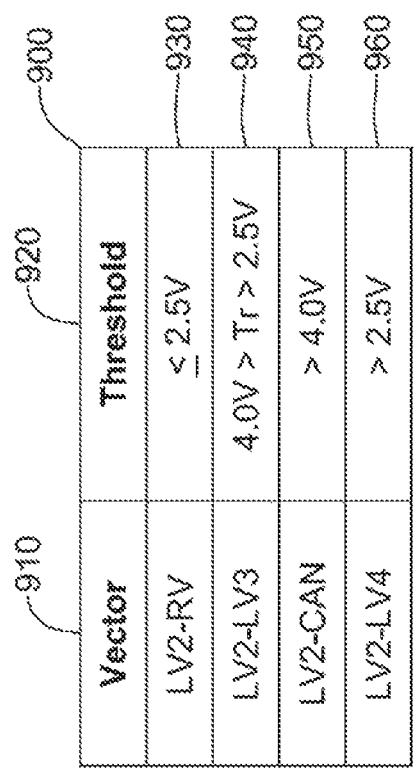
FIG. 9 is an illustrative table of vectors which may be displayed by the implantable medical system of FIG. 1.

After performing any of the above described techniques, device 101 may additionally display results to a user. For example, as described above, device 101 may record results for each of the vectors. Device 101 may additionally communicate such recorded results to an external device, such as external assembly 140, via communications circuits 102 and 142. External assembly 140 may display such results in one or more tables, for example via user interface 145. FIGS. 9 and 10 depict example results that external assembly 140 may display via user interface 145.

The example results shown in FIG. 9 are displayed in a two-column results table 900. The first column is a vector column 910. Vector column 910 may include a listing of all of the vectors in the first set of vectors. In other examples, vector column 910 may include a sub-set of the first set of vectors. The second column is a quick capture threshold column 920. Quick capture threshold column 920 may display results of any of the techniques described with respect to FIGS. 3-8. For example, quick capture threshold column 920 may display a value of a first voltage level $V_1$ that device 101 used in delivering one or more pacing pulses to the heart 115 via the vectors, and whether the capture threshold for each vector was below or above that value. In other examples, quick capture threshold column 920 may display a value of a second voltage level $V_2$ that device 101 used in delivering one or more pacing pulses to heart 115 via the vectors. In still other examples, quick capture threshold column 920 may display a value of a third voltage level $V_3$ that device 101 used in delivering one or more pacing pulses to heart 115 via the vectors.

As one illustrative example, device 101 may have delivered one or more pacing pulses via vector LV2-RV at a first voltage level $V_1$, which was two and a half volts, and determined whether the delivered one or more pacing pulses captured the heart 115 or not. In the illustrative example, device 101 did determine that the one or more delivered pacing pulses captured the heart 115. Accordingly, the cell 930 in results table corresponding to vector LV2-RV in quick capture threshold column 920 includes a less than or equal sign in conjunction with the two and a half volts $V_1$, indicating that the capture threshold for vector LV2-RV is less than or equal to two and a half volts. If the delivered pacing pulse or pulses had not captured the heart 115, cell 930 in results table 900 may display a greater than sign, indicating that the capture threshold for the vector LV2-RV is greater than two and a half volts.

In other examples, the value displayed in quick capture threshold column 920 may be the value of the second voltage level $V_2$. For example, device 101 may first deliver pacing pulses at a first voltage level $V_1$. After determining that the delivered pacing pulse or pulses for a vector captured the heart, device 101 may additionally deliver one or more pacing pulses at a second voltage level $V_2$ and determine whether the delivered pacing pulse or pulses captured the heart. Accordingly, the value and any sign displayed in quick capture threshold column 920 may indicate whether the capture threshold for a corresponding vector is greater than, less than or equal to, or equal to the second voltage level $V_2$. In a similar manner, the value displayed in quick capture threshold column 920 may be the value of the third voltage level $V_3$.

In some examples, quick capture threshold column 920 may contain cells that have different voltage values. For example, if device 101 determined that a delivered pacing pulse or pulses at a first voltage level $V_1$ did not capture the heart for a first vector, then the corresponding cell in quick capture threshold column 920 may include the value of the first voltage level $V_1$ and a greater than sign, such as shown in cell 950. However, if, for a second vector, device 101 determined that one or more pacing pulses delivered at the first voltage level $V_1$ did capture the heart, but one or more pacing pulses delivered at a second voltage level $V_2$ did not capture the heart, the corresponding cell of quick capture threshold column 920 may display a value equal to the second voltage level $V_2$ and a greater than sign, such as shown in cell 960. In other such examples, the corresponding cell may display both the value of the first voltage level $V_1$ and the value of the second voltage level $V_2$, with a less than sign associated with the first voltage level $V_1$ and a greater than sign associated with the second voltage level $V_2$, such as shown in cell 940. This indicates that the capture threshold for the vector is somewhere between the first voltage level $V_1$ and the second voltage level $V_2$. If, for a third vector, device 101 determined that one or more pacing pulses delivered at both first and second voltage levels, $V_1$ and $V_2$, captured the heart 115, the corresponding cell of quick capture threshold column 920 may display a value of the second voltage level $V_2$ in conjunction with a less than or equal to sign, such as shown in cell 930, indicating that the capture threshold for the vector is less than or equal to the second voltage level $V_3$. In examples where device 101 additionally delivers one or more pacing pulses at a third voltage level $V_3$ for one or more of the vectors, corresponding cells may display a value of the third voltage level $V_3$ and a greater than sign or less than or equal to sign, as in the above examples.

The example results in FIG. 10 are displayed in a three-column results table 1000. The first two columns, vector column 1010 and quick capture threshold column 1020 are similar to vector column 910 and quick capture threshold column 920 described with respect to FIG. 9. Threshold column 1030 may display any capture thresholds that device 101 determined, for instance according to any of the techniques described above. For example, for vector LV2-RV, if device 101 determined that one or more pacing pulses delivered at a voltage level $V_2$ of two and a half volts captured heart 115, device 101 may additionally determine a capture threshold. For example, device 101 may successively step down the voltage level and deliver one or more pacing pulses at decreasing voltage levels until determining that one or more delivered pacing pulses at a current voltage level failed to capture the heart 115. As one example, device 101 may determine that a voltage level of 1.2V was the lowest voltage level at which one or more delivered pacing pulses captured heart 115. Accordingly, device 101 may cause this value to be displayed in results table 1000, such as shown in cell 1040. Similarly, if device 101 determines that one or more delivered pacing pulses at the first voltage level $V_1$ captured the heart 115, but delivered pacing pulses at a second voltage level $V_2$ failed to capture the heart 115, device 101 may still determine a capture threshold. As one example, the first voltage level $V_1$ may be four volts and the second voltage level $V_2$ may be two and a half volts, and device 101 may determine the capture threshold to be 2.7V. Accordingly, device 101 may cause this value to be displayed in results table 1000, such as shown in cell 1050.

In some examples, device 101 may not determine a capture threshold for each vector. For example, device 101 may only determine a capture threshold for those vectors where delivering one or more pacing pulses at a second voltage level $V_2$ captured the heart 115. In other examples, device 101 may only determine a capture threshold for those vectors where delivering one or more pacing pulses at a first voltage level $V_1$ captured the heart 115. In still other examples, device 101 may only determine a capture threshold for those vectors where delivering one or more pacing pulses at a third voltage level $V_3$ captured the heart 115. Accordingly, one or more cells of threshold column 1030 may not display any values, such as cells 1060 and 1070. In some examples, device 101 may deliver one or more pacing pulses at a first, second, and/or third voltage level, as in any of the examples described above. Device may then cause results to be displayed in results table 1000, without the third column 1030 filled in for any of the vectors. Then, a user may select one or more of the vectors displayed in results table 1000, and device 101 may then determine a capture threshold for only the selected vectors.

As described above, a number of the parameters by which device 101 operates may be configurable by a user. FIG. 11 depicts an example GUI 1116 that may be displayed to a user by an external device, for example external assembly 140. GUI 1116 may include a table 1136 which lists a number of vectors 1138 in addition to various parameters for each vector, for example, an RV-LV delay in RV-LV delay column 1140, an impedance in impedance column 1142, and a phrenic nerve stimulation threshold in PS threshold column 1144. Table 1136 may additionally include quick capture threshold column 1146. Quick capture threshold column 1146 may be similar to quick capture threshold column 920 or 1020 of FIGS. 9 and 10. In some examples, table 1136 may include an additional column which displays threshold values as described with respect to column 1030 in FIG. 10.

GUI 1116 may additionally include $1^{st}$ voltage level box 1120, $2^{nd}$ voltage level box 1122, and/or $3^{rd}$ voltage level box 1124. When so provided, a user may input a value or alter an existing value in any of boxes 1120, 1122, and/or 1124 before device 101 delivers any pacing pulses to the vectors 1138. Accordingly, device 101 may configure the first voltage level $V_1$, second voltage level $V_2$, and/or third voltage level $V_3$ with the values in boxes 1120, 1122, and/or 1133. In examples where device 101 does not deliver pacing pulses via a third voltage level $V_3$, GUI 1116 may omit displaying box 1124. Each box may have a maximum and/or minimum allowable value. If the user attempts to enter a value in any of boxes 1120, 1122, and/or 1124 greater than the maximum allowable value for the box and/or less than the minimum allowable value, GUI 1116 may display a new window with a warning to a user. Additionally, device 101 may configure a corresponding voltage level with the maximum/minimum allowable value, as described in previous examples.

In examples where device 101 uses one or more step values, and such step values are configurable, GUI 1116 may additionally display $1^{st}$ step value box 1126 and/or $2^{nd}$ step value box 1128. As with boxes 1120, 1122, and 1124, a user may input a value or alter a value in either or both of boxes 1126 and 1128. Device 101 may then configure a first step value and/or a second step value with the value of boxes 1126 and 1128. In some cases, boxes 1126 and 1128 may have maximum and/or minimum allowable values. If user attempts to enter a value in any of boxes 1126 and 1128 greater than the maximum allowable value for the box and/or less than the minimum allowable value, GUI 1116 may display a new window with a warning to a user. Additionally, device 101 may configure a corresponding step value with the maximum/minimum allowable value.

In some cases, the device 101 may use a relatively high voltage such as 7.5V to determine an RV-LV delay parameter, an impedance parameter, and/or a phrenic nerve stimulation parameter for each vector, and may enter those parameters into the RV-LV delay column 1140, the impedance column 1142, and/or the PS threshold column 1144 of table 1136. In some cases, the user may sort the vectors by selecting a sort button for a particular column. In the example shown in FIG. 10, the user has selected the sort button 1144a, which places all of the vectors that produced phrenic stimulation at 7.5 volts at the bottom of the table 1136, as these are less desirable vectors. The user may then select the Start LV Threshold Search button 252 to start any of the capture threshold algorithms described herein. In some instances, and before selecting the Start LV Threshold Search button 252, the user may select certain vectors 1138, and then select the Start LV Threshold Search button 252 to perform a capture threshold algorithm as described herein on only the selected vectors.

Figure 12:
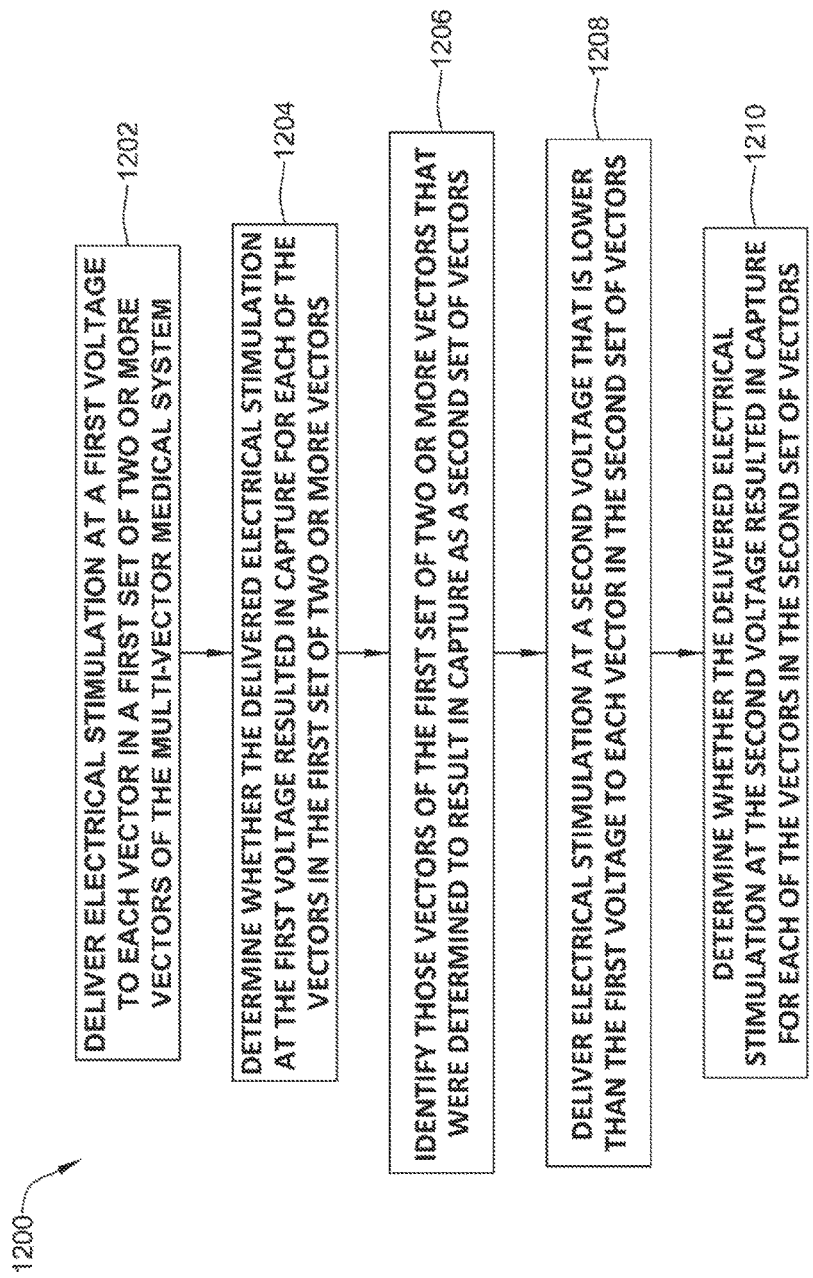
FIG. 12 is a flow diagram of an illustrative method that may be implemented by an implantable medical device system such as the implantable medical system of FIG. 1.

FIG. 12 is a flow diagram of an illustrative method that may be implemented by an implantable medical device system such as shown in any of FIGS. 1 and 2. Although the method of FIG. 12 is described with respect to the medical device system 100 of FIG. 1, the method of FIG. 12 may be performed by any suitable medical device system.

In some examples, an implantable medical device, for example implantable medical device 101 of system 100, may be implanted in a patient with one or more leads extending into heart 115. Device 101 may be configured to sense cardiac events and deliver electrical stimulation to heart 115. In some examples, device 101 may be configured to deliver electrical stimulation at a first voltage to each vector in a first set of two or more vectors of the multi-vector medical system, as shown at 1202. Device 101 may additionally be configured to determine whether the delivered electrical stimulation at the first voltage resulted in capture for each of the vectors in the first set of two or more vectors, as shown at 1204. For example, device 101 may sense for cardiac electrical signals after delivering electrical stimulation. If device 101 senses cardiac electrical signals, or a particular pattern of cardiac electrical signals that indicated capture, device 101 may determine that the delivered electrical stimulation resulted in capture. Device 101 may further be configured to identify those vectors of the first set of two or more vectors that were determined to result in capture into a second set of vectors, as shown at 1206. Device 101 may then deliver electrical stimulation at a second voltage that is lower than the first voltage to each vector in the second set of vectors, as shown at 1208. Next, device 101 may determine whether the delivered electrical stimulation at the second voltage resulted in capture for each of the vectors in the second set of vectors, as shown at 1210.

Figure 13:
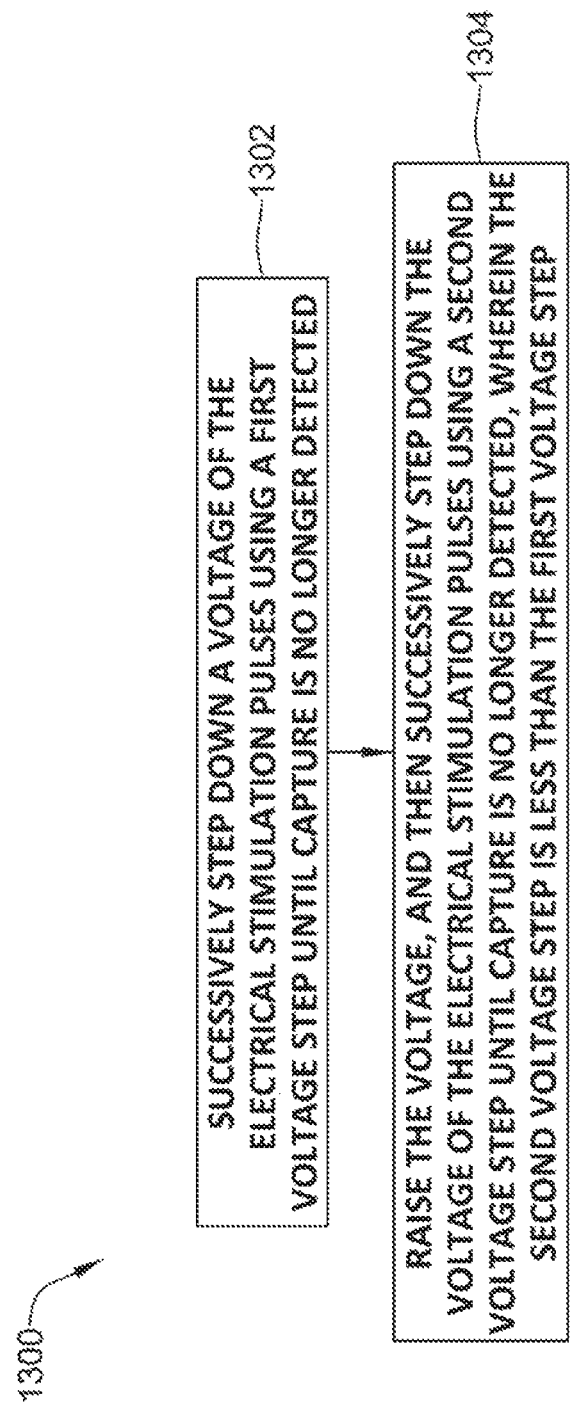
FIG. 13 is a flow diagram of another illustrative method that may be implemented by an implantable medical device system such as the implantable medical system of FIG. 1.

FIG. 13 is a flow diagram of another illustrative method that may be implemented by an implantable medical device system such as shown in any of FIGS. 1 and 2. Although the method of FIG. 13 will be described with respect to the medical device system 100 of FIG. 1, the method of FIG. 13 may be performed by any suitable medical device system.

In some examples, an implantable medical device, for example implantable medical device 101 of system 100, may be implanted in a patient with one or more leads extending into heart 115. Device 101 may be configured to sense cardiac events and deliver electrical stimulation to heart 115. In some examples, device 101 may be configured to successively step down a voltage of the electrical stimulation pulses using a first voltage step until capture is no longer detected, as shown at 1302. Device 101 may additionally be configured to raise the voltage, and then successively stepping down the voltage of the electrical stimulation pulses using a second voltage step until capture is no longer detected, wherein the second voltage step is less than the first voltage step, as shown at 1304.

FIG. 14 is another flow diagram of an illustrative method that may be implemented by an implantable medical device system such as shown in any of FIGS. 1 and 2. Although the method of FIG. 14 will be described with respect to the medical device system 100 of FIG. 1, the method of FIG. 14 may be performed by any suitable medical device system.

In some examples, an implantable medical device, for example implantable medical device 101 of system 100, may be implanted in a patient with one or more leads extending into heart 115. Device 101 may be configured to sense cardiac events and deliver electrical stimulation to heart 115. Device 101 may be configured to receive a user defined first voltage level V1, as shown at 1402. For example, a user may enter input, such as through user interface 145, indicating a voltage level V1. In some examples, device 101 may cause a GUI to be displayed at user interface 145, such as GUI 1116, which provides input boxes for a user to enter input. In the example shown, a user defined first voltage level may be entered via input box 1120 of GUI 1116. Once entered, device 101 may deliver electrical stimulation at the user defined first voltage level to each vector in a first group of vectors of the multi-vector medical system, as shown at 1404. Device 101 may then be configured to identify a second group of vectors that includes the vectors of the first group of two or more vectors for which the delivered electrical stimulation at the user defined first voltage level V1 resulted in capture, as shown at 1406. For instance, in some examples, device 101 may automatically determine whether the delivered electrical stimulation captured the heart. In other examples, device 101 may receive input from a user indicating whether the delivered electrical stimulation captured the heart.

After identifying the second group of vectors, device 101 may perform a test on each of the vectors in the identified second group of vectors, as shown at 1408. In some examples, device 101 may perform a traditional capture threshold test on each vector in the second group of vectors. Device 101 may use the user defined first voltage level V1 as the initial voltage level for the traditional capture threshold test. In other examples, device 101 may use a different voltage level, such as a voltage level that is less than or greater than the user defined first voltage level V1 as the initial voltage level for the traditional capture test. In some instances, the initial voltage level for the traditional capture test may be user defined. In some examples, the test may include any of the techniques disclosed herein with respect to FIGS. 3-8, 12, and 13.

In some cases, the first voltage level V1 may be set at a level that is expected to be above the capture threshold for all of the vectors in the first group of vectors (e.g. 7 volts). In other instances, the first voltage level V1 may be set to a level that is deemed by the user to be an acceptable voltage level for subsequent long term pacing (e.g. 3 volts), and the system may determine which of the vectors of the first group of vectors do not capture the heart at that voltage level and may automatically eliminate those vectors from the second group of vectors.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method for determining a capture threshold for one or more vectors of a multi-vector medical system, the method comprising:
   receiving a first subset of vectors from among available vectors in the multi-vector system;
   delivering electrical stimulation at a first voltage to each vector in the first subset of vectors;
   determining whether the delivered electrical stimulation at the first voltage resulted in capture for each of the vectors in the first subset of vectors;
   delivering electrical stimulation at a second voltage that is lower than the first voltage to a second subset of vectors having less vectors than the first subset of vectors and selected from the first subset of vectors; and
   determining a capture threshold for each vector of the second subset of vectors.

2. The method of claim 1 further including iteratively delivering electrical stimulation at successively lower voltages and determining at each voltage whether the delivered electrical stimulation resulted in capture, until the capture threshold is determined.

3. The method of claim 1, wherein the first voltage is user defined.

4. The method of claim 1, including raising the first voltage and returning to the first delivering step in response to the delivered electrical stimulation at the first voltage not resulting in capture for any of the vectors in the first set of two or more vectors.

5. The method of claim 1, wherein the second subset of vectors includes vectors of the first subset of vectors that resulted in capture at the first voltage and excludes vectors of the first subset of vectors that failed to result in capture at the first voltage.

6. The method of claim 1, wherein the first voltage is between 1.5 and 4.5 volts.

7. The method of claim 1, wherein the first voltage is between 2.0 and 3.5 volts.

8. The method of claim 1, wherein the first subset of stimulation vectors includes two or more stimulation vectors of the multi-vector medical system and includes less than all of the stimulation vectors of the multi-vector medical system.

9. The method of claim 1, further including selecting the first subset as two or more vectors of the multi-vector medical system.

10. The method of claim 9, further including:
    generating one or more parameters for each of the available vectors of the multi-vector medical system; and
    selecting the first set of two or more vectors from all available vectors of the multi-vector medical system based, at least in part, on the one or more generated parameters.

11. The method of claim 10, wherein the one or more parameters include an impedance, a time delay, or a phrenic stimulation value.

12. The method of claim 1, further including:
    identifying those vectors of the second set of vectors that were determined to result in capture as a third set of vectors;
    delivering electrical stimulation at a third voltage that is lower than the second voltage to each vector in the third set of vectors; and
    determining whether the delivered electrical stimulation at the third voltage resulted in capture for each of the vectors in the third set of vectors.

13. The method of claim 12, further including, for each vector in the third set of vectors, repeatedly delivering electrical stimulation at successively lower voltages and determining at each voltage whether the delivered electrical stimulation resulted in capture, until the capture threshold is determined.

14. A system comprising:
    a plurality of stimulation vectors, wherein a stimulation vector includes multiple stimulation electrodes;

a pulse generator configured to deliver electrical stimulation pulses using each of the stimulation vectors;
a controller coupled to the pulse generator, wherein the controller is configured to:
select a first subset of vectors from among the plurality of stimulation vectors;
deliver electrical stimulation at a first voltage to each vector in the first subset of vectors;
determine whether the delivered electrical stimulation at the first voltage resulted in capture for each of the vectors in the first subset of vectors;
deliver electrical stimulation at a second voltage that is lower than the first voltage to a second subset of vectors having less vectors than the first subset of vectors and selected from the first subset of vectors; and
determine a capture threshold for each vector of the second subset of vectors.

15. The system of claim 14, wherein the controller is configured to initiate a measurement of one or more parameters for each of the plurality of stimulation vectors; and select the first subset of vectors from among the plurality of stimulation vectors according to the one or more measured parameters.

16. The system of claim 15, wherein the controller is configured to initiate a measurement of one or more of lead impedance, RV-LV delay, and a phrenic nerve stimulation threshold and select the first subset of vectors from among the plurality of stimulation vectors according to the one or more measured parameters.

17. The system of claim 14, including a communication circuit operatively coupled to the controller and configured to communicate with a separate device, wherein the controller is configured to select the first subset of vectors according to stimulation vector information received from the separate device.

18. A system comprising an implantable medical device and an external device, wherein the implantable medical device is configured for coupling to a plurality of stimulation vectors,
wherein the external device includes: a first communication circuit configured to communicate with the implantable device; and a user interface, wherein the external assembly is configured to receive a selection of a first subset of vectors from among the plurality of vectors via the user interface and enable delivery of electrical stimulation using the first subset of vectors; and
wherein the implantable medical device includes: a second communication circuit configured to communicate with the external device; a pulse generator configured to deliver electrical stimulation pulses using each of the stimulation vectors; a controller coupled to the pulse generator and the second communication circuit, wherein the controller is configured to:
deliver electrical stimulation at a first voltage to each vector in the first subset of vectors;
determine whether the delivered electrical stimulation at the first voltage resulted in capture for each of the vectors in the first subset of vectors;
deliver electrical stimulation at a second voltage that is lower than the first voltage to a second subset of vectors having less vectors than the first subset of vectors and selected from the first subset of vectors; and
determine a capture threshold for each vector of the second subset of vectors.

19. The system of claim 18, wherein the controller is configured to communicate an indication of the capture threshold for each vector of the second subset of vectors to the external device and the external device is configured to present the second subset of vectors and the capture thresholds to a user.

20. The system of claim 18, wherein the external device is configured to initiate a measurement of one or more parameters for each of the plurality of stimulation vectors by the implantable medical device; and select the first subset of vectors from among the plurality of stimulation vectors according to the one or more measured parameters.

* * * * *